United States Patent
Ogawa

(10) Patent No.: US 10,401,299 B2
(45) Date of Patent: Sep. 3, 2019

(54) IMAGE CAPTURING APPARATUS AND INSPECTION APPARATUS AND INSPECTION METHOD

(71) Applicant: NuFlare Technology, Inc., Yokohama (JP)

(72) Inventor: Riki Ogawa, Kanagawa (JP)

(73) Assignee: NuFlare Technology, Inc., Yokohama (JP)

( * ) Notice: Subject to any disclaimer, the term of this patent is extended or adjusted under 35 U.S.C. 154(b) by 486 days.

(21) Appl. No.: 14/677,039

(22) Filed: Apr. 2, 2015

(65) Prior Publication Data
US 2015/0285744 A1    Oct. 8, 2015

(30) Foreign Application Priority Data

Apr. 4, 2014 (JP) .................................. 2014-078090
Mar. 31, 2015 (JP) .................................. 2015-073512

(51) Int. Cl.
    *G01N 21/88*        (2006.01)
    *G01N 21/95*        (2006.01)
    (Continued)

(52) U.S. Cl.
    CPC ..... *G01N 21/8806* (2013.01); *G01N 21/9501* (2013.01); *G02B 27/283* (2013.01);
    (Continued)

(58) Field of Classification Search
    CPC .......... G01N 21/88; G01N 21/95; G06T 7/00; G02B 27/283
    (Continued)

(56) References Cited

U.S. PATENT DOCUMENTS 5,364,819 A * 11/1994 Dexter .................... C03C 3/247
                                              252/301.4 H
5,477,309 A * 12/1995 Ota ........................... G03F 9/70
                                                    355/53

(Continued)

FOREIGN PATENT DOCUMENTS

DE    102012203947 A1 * 3/2013 ............. G01N 21/21
DE    102012203947 A1 * 3/2013 ............. G01N 21/21
(Continued)

OTHER PUBLICATIONS

New PVLAS results and limits on magnetically induced optical rotation and ellipticity in vacuum, Phys. Rev D77:032006, 2008, DOI: 10.1103/PhysRevD.77.032006, arXiv:0706.3419 [hep-ex]; Please refer to the web page found at https://arxiv.org/abs/0706.3419.*

(Continued)

*Primary Examiner* — Richard A Hansell, Jr.
(74) *Attorney, Agent, or Firm* — Oblon, McClelland, Maier & Neustadt, L.L.P.

(57) ABSTRACT

An imaging capturing apparatus comprising, a light source, a polarizing beam splitter configured to illuminate a target with light from the light source, a sensor configured to capture an image of the inspection target by incidence of light reflected from the target through the polarizing beam splitter, and a Faraday rotator provided between the polarizing beam splitter and the target and disposed away from the polarizing beam splitter such that a Faraday rotation angle in the polarizing beam splitter is within a range of an angle equal to or larger than −0.5 degrees and an angle equal to or smaller than 0.5 degrees.

20 Claims, 13 Drawing Sheets

(51) Int. Cl.
  *G02B 21/00* (2006.01)
  *G02B 27/28* (2006.01)
(52) U.S. Cl.
  CPC ... *G02B 27/286* (2013.01); *G01N 2201/0636* (2013.01); *G01N 2201/0683* (2013.01); *G01N 2201/06113* (2013.01); *G02B 21/0016* (2013.01)
(58) Field of Classification Search
  USPC .......................................................... 348/126
  See application file for complete search history.

(56) References Cited

U.S. PATENT DOCUMENTS

| | | | |
|---|---|---|---|
| 6,768,543 B1 * | 7/2004 | Aiyer | G01N 21/21 356/237.1 |
| 2005/0213103 A1 | 9/2005 | Everett et al. | |
| 2006/0152716 A1 * | 7/2006 | Meeks | G01B 11/0616 356/237.2 |
| 2011/0134520 A1 * | 6/2011 | Goruganthu | G02B 21/0016 359/386 |
| 2012/0002860 A1 * | 1/2012 | Sakai | G06T 7/001 382/149 |
| 2012/0327503 A1 * | 12/2012 | Manassen | G01J 1/4257 359/291 |
| 2013/0120824 A1 * | 5/2013 | Ono | G02F 1/09 359/284 |
| 2013/0121617 A1 | 5/2013 | Serrels et al. | |
| 2015/0054941 A1 | 2/2015 | Ogawa | |
| 2016/0004167 A1 | 1/2016 | Kohl | |
| 2016/0033586 A1 * | 2/2016 | Hakenes | G01R 33/07 324/251 |

FOREIGN PATENT DOCUMENTS

| | | | | |
|---|---|---|---|---|
| JP | 2004198286 A | * | 7/2004 | ............. G01N 21/21 |
| JP | 2004198286 A | * | 7/2004 | ............. G01N 21/21 |
| JP | 4236825 | | 3/2009 | |
| TW | 200811610 A | | 3/2008 | |
| TW | 201139023 A1 | | 11/2011 | |
| TW | 201303258 A1 | | 1/2013 | |
| TW | 201329438 A1 | | 7/2013 | |

OTHER PUBLICATIONS

Pereda-Cubián et al. "Evaluation of the magneto-optical effect in biological tissue models using optical coherence tomography" JBO Letters, vol. 12(6), Nov./Dec. 2007.*
Kim et al. "Determination of the infrared complex magnetoconductivity tensor in itinerant ferromagnets from Faraday and Kerr measurements", Physical Review B 75, 214416 (2007) (Year: 2007).*
Yoshida et al. "Influence of the stray magnetic field generated by the Faraday isolator on SOS mirror actuators", Laser Interferometer Gravitational Wave Observatory, LIGO-T970149-00-D, Nov. 2, 1996 (Year: 1996).*
Kim et al. "Measurement of the infrared complex Faraday angle in semiconductors and insulators", vol. 28, No. 2, J. Opt. Soc. Am. B, pp. 199-207, Feb. 2011 (Year: 2011).*
Pereda-Cubian et al. "Evaluation of the magneto-optical effect in biological tissue models using optical coherence tomography" JBO Letters, vol. 12(6), Nov./Dec. 2007 (Year: 2007).*
New PVLAS results and limits on magnetically induced optical rotation and ellipticity in vacuum, Phys. Rev D77:032006, 2008, DOI: 10.1103/PhysRevD.77.032006, arXiv:0706.3419 [hep-ex]; Please refer to the web page found at https://arxiv.org/abs/0706.3419 (Year: 2008).*
Office Action dated May 4, 2016 in Korean Patent Application No. 10-2015-0046244 (with English language translation).
Combined Taiwanese Office Action and Search Report dated Feb. 17, 2016 in Patent Application No. 104109385 (with English language translation).

* cited by examiner

IMAGE CAPTURING APPARATUS AND INSPECTION APPARATUS AND INSPECTION METHOD

CROSS-REFERENCE TO THE RELATED APPLICATION

The entire disclosure of Japanese Patent Application No. 2014-078090, filed on Apr. 4, 2014, and 2015-073512 filed on Mar. 31, 2015, including specifications, claims, drawings, and summaries, on which the Convention priority of the present application is based, are incorporated herein in their entirety.

FIELD OF THE INVENTION

The present invention relates to an Image Capturing Apparatus and an Inspection Apparatus and Inspection Method.

Recently, with an increasing integration degree of a semiconductor device, the dimensions of individual elements have become finer, and the widths of wiring and gate constituting each element have also become finer.

A process of transferring an original plate (known as a mask or a reticle, hereinafter collectively referred to as a mask) to a photosensitive resin to fabricate a wafer is fundamental to the production of a semiconductor integrated circuit. Repeating this fundamental process produces the semiconductor integrated circuit.

An exposure apparatus called a stepper or a scanner is used in the transfer process. In the exposure apparatus, light is used as a transfer light source, and a circuit pattern on the reticle is projected onto the wafer while reduced from about one-fourth to about one-fifth size. In order to increase the integration degree of the semiconductor integrated circuit, it is necessary to improve resolution performance in the transfer process. If NA is defined as a numerical aperture of an imaging optical system, and $\lambda$ is defined as a wavelength of the light source, a resolution dimension is proportional to ($\lambda$/NA). Accordingly, higher exposure resolution can be achieved by increasing the numerical aperture NA or decreasing the wavelength $\lambda$.

EUV (Extreme Ultraviolet) lithography and nanoimprint lithography (NIL) have attracted attention as technologies for forming fine patterns on a semiconductor wafer. Since the EUV lithography uses extreme ultraviolet light as a light source to transfer patterns of EUV mask onto the wafer, it is possible to form finer patterns on the wafer than a conventional exposure apparatus using ArF light. In the nanoimprint lithography, a fine pattern is formed in a resist by pressuring a template having a nanometer-scale fine structure to the resist on the wafer. In any technology, a pattern formed in the EUV mask and the template being an original plate is finer when compared with conventional ArF lithography. Thus, high inspection accuracy is required for the inspection thereof.

Since LSI manufacturing requires a tremendous amount of manufacturing cost, it is crucial to improve a production yield. A defect of a circuit pattern formed on of a mask or template can be cited as a large factor that reduces a production yield of the semiconductor element. It is also necessary to detect the defect of the extremely small pattern in an inspection process. Japanese Patent Number 4236825 discloses an inspection apparatus that can detect fine defects in the mask.

In the mask inspection process in the inspection apparatus, the mask is illuminated with the light while the mask is moved with a mask stage; the light transmitted through the mask or reflected therefrom is imaged on a sensor through the optical system. An image captured by the sensor is transmitted as measurement data to the comparison circuit. In the comparison circuit, after performing position adjustment of images, the obtained optical image is compared to a reference image, namely, an image that is compared to the optical image of a pattern in order to detect a defect, and a place where a difference between the optical image and the reference image exceeds a threshold is detected as a defect in accordance with an appropriate algorithm. If there is no match between the compared images, it is determined that there is a pattern defect.

In the inspection process, it is necessary to ensure that a sufficient amount of light is incident to the sensor. If the amount of the light is insufficient, degradation of inspection accuracy and lengthening of inspection time are caused. In an Inspection Apparatus, light emitted from a light source is reflected by a half mirror, a mask is irradiated with the light, the light reflected by the mask is transmitted through the half mirror, and the light is incident to a sensor to capture an optical image. At this point, the light reflected by the half mirror, which is used only as the illumination light for the mask, decreases the amount of the light to a half of the amount of light emitted from the light source. Then, the light transmitted through the half mirror in the light reflected from the mask, which is used as the light incident to the sensor, further decreases the amount of the light by a half again. That is, in the reflective optical illumination system, the light incident to the sensor becomes a quarter of the amount of light emitted from the light source.

In the reflective optical illumination system, a reduction in the amount of light from a light source can be improved by using a Faraday rotator. However, since the Faraday rotator generates a strong magnetic field therearound, a Faraday rotation effect may be generated in elements adjacent to the Faraday rotator.

The invention has been devised to solve the problem described above. An object of the present invention is to provide an image capturing apparatus including a Faraday rotator, capable of minimizing the influence of the Faraday rotation effect on elements disposed around the Faraday rotator. Another object of the invention is to provide an inspection apparatus and an inspection method, for being able to minimally restrain the degradation of the amount of light in the reflective illumination optical system, using the image capturing apparatus.

Other advantages and challenges of the present invention are apparent from the following description.

SUMMARY OF THE INVENTION

According to one aspect of the present invention, an imaging capturing apparatus includes a light source, a polarizing beam splitter configured to illuminate a target with light from the light source, a sensor configured to capture an image of the inspection target by incidence of light reflected from the target through the polarizing beam splitter, and a Faraday rotator provided between the polarizing beam splitter and the target and disposed away from the polarizing beam splitter such that a Faraday rotation angle in the polarizing beam splitter is within a range of an angle equal to or larger than −0.5 degrees and an angle equal to or smaller than 0.5 degrees.

According to another aspect of the present invention, an inspection apparatus includes an illumination optical system including a light source configured to emit light having a predetermined wavelength, a polarization beamsplitter which reflects the light emitted from the light source, a half-wavelength plate which transmits the light reflected by the polarization beamsplitter, and a Faraday rotator which is configured between the half-wavelength plate and a sample which is an inspection target and transmits the light transmitted through the half-wavelength plate, configured to illuminate the sample by the light including a polarization plane having an angle except an angle within a range of an angle equal to or larger than −0.5 degrees and an angle equal to or smaller than 0.5 degrees, and a range of an angle equal to or larger than −85 degrees and an angle equal to or smaller than 95 degrees with respect to a repetitive direction of a repetitive pattern formed in the sample, a sensor configured to capture an optical image of a pattern formed in the sample, an imaging optical system configured to form an image of the light reflected by the sample onto the sensor by causing the light to be transmitted through the half-wavelength plate, the Faraday rotator, and the polarization beamsplitter, an image processor configured to obtain a gradation value in each pixel with respect to the optical image and acquire (1) a rotation angle of the polarization plane of the light rotated by the Faraday rotator for minimizing a standard deviation of the gradation value, or
(2) a rotation angle for minimizing a value which is obtained by dividing the standard deviation of the gradation values of a plurality of optical images obtained by changing the rotation angle, by a square root of an average gradation value obtained from the gradation value, an angle controller that applies a magnetic field to the Faraday rotator so as to obtain the rotation angle acquired by the image processor, and a defect detector that detects a defect of the sample based on an optical image which is captured while the magnetic field is applied to the Faraday rotator.

The predetermined wavelength of the light from the light source and a numerical aperture of an objective lens through which the sample is illuminated with the light transmitted through the Faraday rotator defines a resolution limit. The resolution limit is a value at which the pattern is not resolved. The Faraday rotator is disposed away from the polarizing beam splitter such that a Faraday rotation angle in the polarizing beam splitter is within a range of an angle equal to or larger than −0.5 degrees and an angle equal to or smaller than 0.5 degrees.

According to other aspect of the present invention, an inspection method includes reflecting light emitted from the light source which emits the light having a predetermined wavelength by a polarization beamsplitter. The light is transmitted through a half-wavelength plate and a Faraday rotator. The light including a polarization plane having an angle except an angle within a range of an angle equal to or larger than −0.5 degrees and an angle equal to or smaller than 0.5 degrees, and a range of an angle equal to or larger than −85 degrees and an angle equal to or smaller than 95 degrees with respect to a repetitive direction of a repetitive pattern formed in a sample which is an inspection target, is formed. The light transmitted through the Faraday rotator is converged by an objective lens to be illuminated the sample. The light reflected by the sample is transmitted through the Faraday rotator, the half-wavelength plate, and the polarization beamsplitter. The light is imaged on a sensor to capture an optical image of a pattern formed in the sample. A gradation value is obtained in each pixel with respect to the optical image. (1) A rotation angle of the polarization plane of the light rotated by the Faraday rotator for minimizing a standard deviation of the gradation value, or (2) a rotation angle for minimizing a value which is obtained by dividing the standard deviation of the gradation values of a plurality of optical images obtained by changing the rotation angle, by a square root of an average gradation value obtained from the gradation value, is acquired. A magnetic field is applied to the Faraday rotator such that the acquired rotation angle is obtained. A defect of the sample is detected based on the optical image which is captured while the magnetic field is applied to the Faraday rotator. The predetermined wavelength of the light from the light source and a numerical aperture of the objective lens defines a resolution limit, wherein the resolution limit is a value at which the pattern is not resolved. The Faraday rotator is disposed away from the polarizing beam splitter such that a Faraday rotation angle in the polarizing beam splitter is within a range of an angle equal to or larger than −0.5 degrees and an angle equal to or smaller than 0.5 degrees.

DETAILED DESCRIPTION OF THE EMBODIMENT

Figure 1:
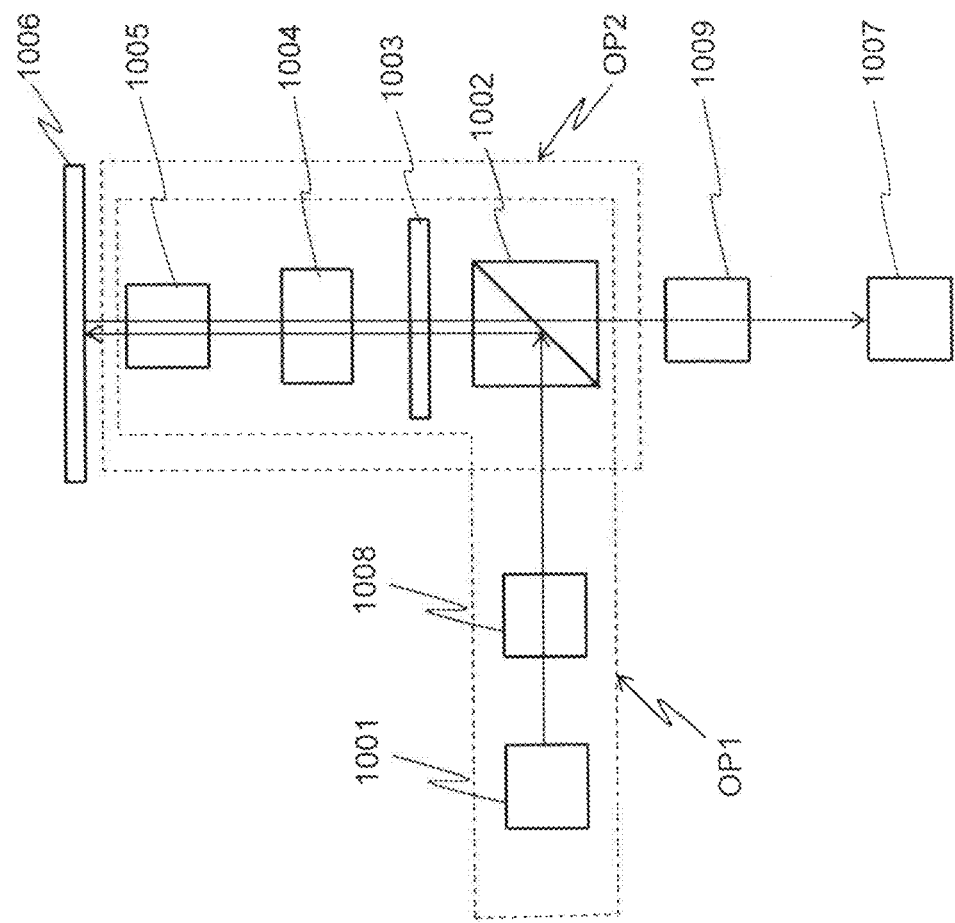
FIG. 1 illustrates an example of a configuration of the image capturing apparatus according to the present embodiment.

FIG. 1 illustrates an example of a configuration of an image capturing apparatus according to the present embodiment. The image capturing apparatus includes an illumination optical system OP1 that illuminates a mask 1006, a sensor 1007 that captures an image of a pattern of the mask 1006, and an imaging optical system OP2 that images the light reflected from the mask 1006 onto the sensor 1007.

The illumination optical system OP1 includes a light source 1001, a beam shaping optical system 1008, a polarization beamsplitter 1002, a half-wavelength plate 1003, a Faraday rotator 1004, and an objective lens 1005. The beam shaping optical system 1008 includes an expander lens that expands a beam, an integrator lens that increases the uniformity of the light to the surface, and a relay lens in which a magnification is set such that a mask surface is illuminated with the beam of a desired size.

The imaging optical system OP2 includes the objective lens 1005, the Faraday rotator 1004, the half-wavelength plate 1003, and the polarization beamsplitter 1002, and an imaging optical system 1009. The imaging optical system 1009 includes a lens group that images the mask onto a sensor surface with the desired magnification. The polarization beamsplitter 1002, the half-wavelength plate 1003, the Faraday rotator 1004, and the objective lens 1005 are shared by the illumination optical system OP1 and the imaging optical system OP2.

A laser light source can be used as the light source 1001 shown in FIG. 1. A light source that emits DUV (Deep Ultraviolet Radiation) light is preferably used in the present embodiment. This enables the inspection to be performed without generating the throughput degradation that becomes troublesome when an EB (Electron Beam) is used as a light source.

Generally the light emitted from the laser light source is linearly polarized light. In the present embodiment, the inspection is performed while the mask 1006 that is an inspection target is illuminated with the linearly polarized light. Therefore, an optical image is obtained having a directionless resolution characteristic. In the present embodiment, the linearly polarized light may be changed into circularly-polarized light, and the inspection target may be illuminated with the circularly-polarized light. By using the circularly polarized light, it is possible to obtain an optical image having no directionality in resolution characteristics. Also, when an inspection target is illuminated with the circularly polarized light, the light emitted from the light source may be transmitted through a quarter-wavelength plate before illuminating the inspection target.

In the illumination optical system OP1 shown in FIG. 1, the linearly polarized light emitted from the light source 1001 is reflected by the polarization beamsplitter 1002, and is incident to the Faraday rotator 1004 through the half-wavelength plate 1003.

The polarizing beam splitter 1002 can be, for example, a cube-shaped beam splitter in which a polarizing film is coated and adhered to an inclined surface of a 45-degrees right-angle prism.

The Faraday rotator 1004 includes an optical material 1004a that transmits the light, and a coil 1004b that is wound around the optical material 1004a. A material having high transmittance to the light emitted from the light source 1001 is used as the optical material 1004a. For example, in the case that the light source 1001 emits the DUV light, a material, such as SiO2, CaF2, and MgF2, which has the transmittance to ultraviolet light, is used as the optical material 1004a. The coil 1004b is wound such that passage of a current applies a magnetic field to the optical material 1004a in a direction parallel to a traveling direction of the light.

The Faraday rotator 1004 rotates a polarization plane of the light by a Faraday effect. As used herein, the Faraday effect means a phenomenon in which, when the linearly polarized light is incident to an optical material to apply the magnetic field in the same direction as the traveling direction of the light, a deviation is generated between phase velocities of two components (right-handed circularly-polarized light and left-handed circularly-polarized light) of the linearly polarized light, and therefore the polarization plane of the light (linearly polarized light) outgoing from the optical material rotates by a phase difference at an exit of the Faraday rotator 1004, that is, the exit of the light incident into the Faraday rotator.

Figure 2:
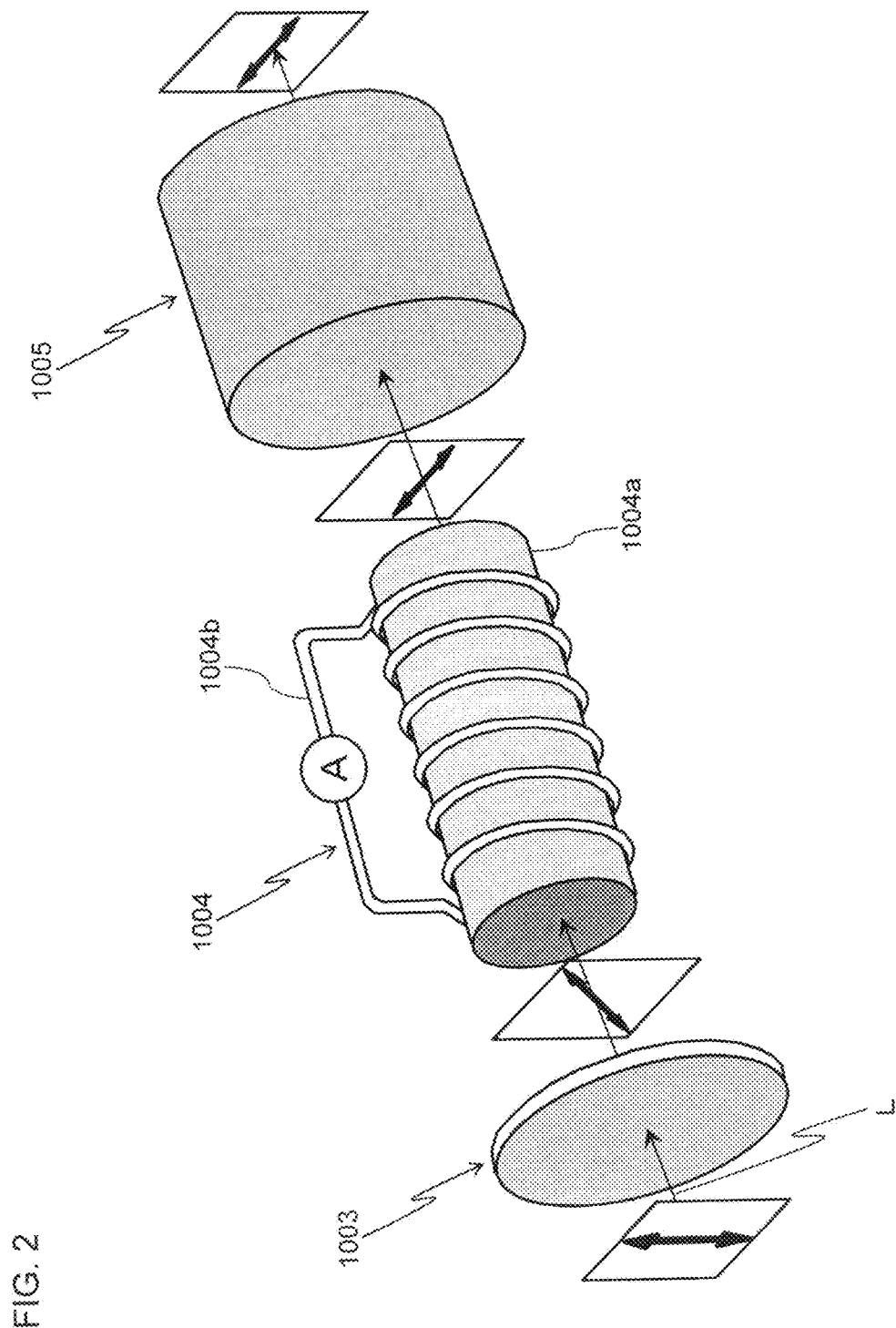
FIG. 2 illustrates a state in which the polarization plane of the light rotates.
Figure 3:
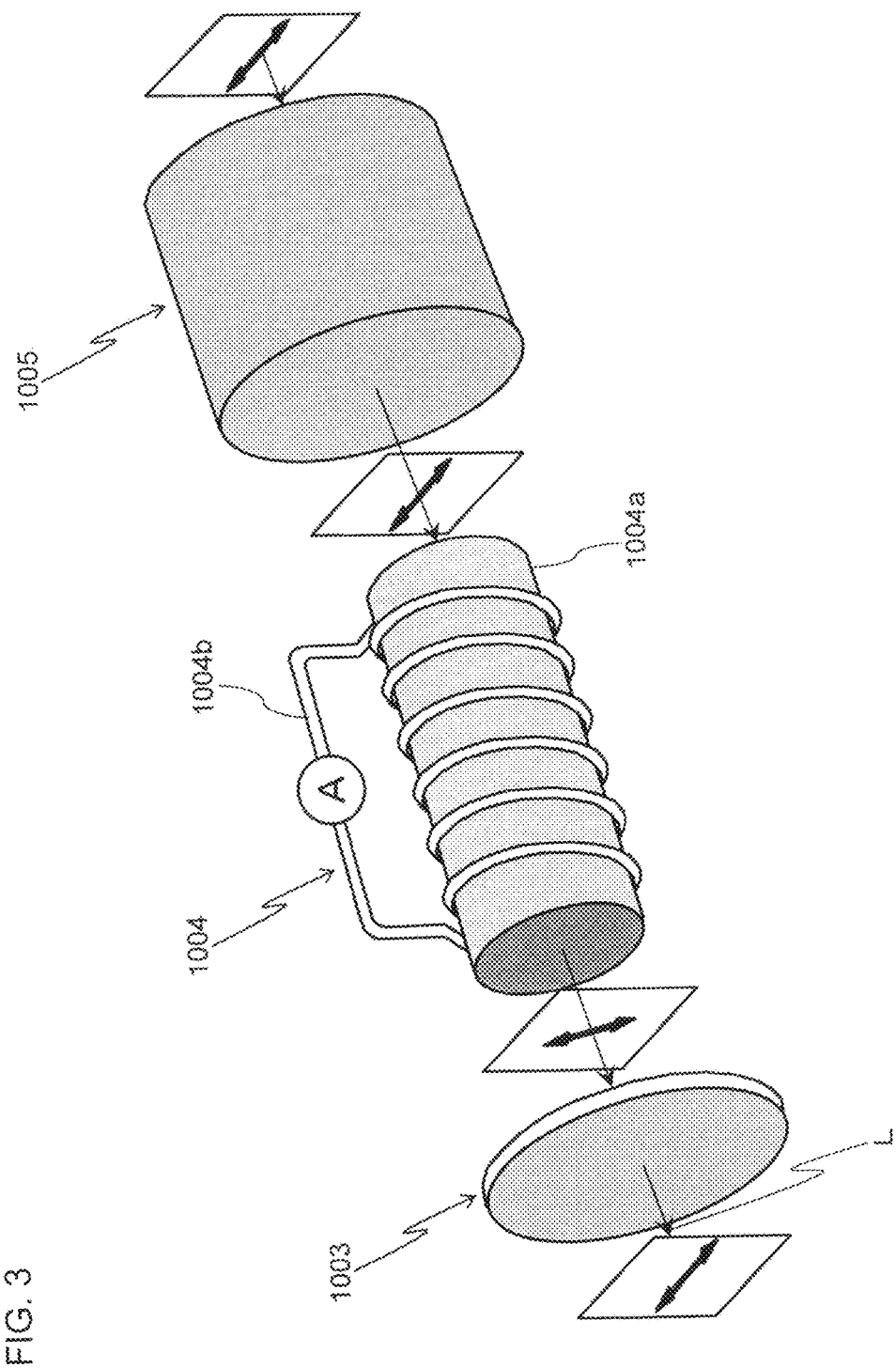
FIG. 3 illustrates a state in which the polarization plane of the light rotates.

In the present embodiment, preferably the polarization plane of the light rotates by 90 degrees as a result of transmitting back and forth through the Faraday rotator 1004. That is, preferably the magnetic field is applied to the optical material such that the polarization plane of the light rotates by 90 degrees as a result of transmitting back and forth. FIGS. 2 and 3 illustrate a state in which the polarization plane of the light rotates. In FIGS. 2 and 3, the same components are designated by the same numerals as that of FIG. 1.

In the example of FIG. 2, a linearly polarized light L is transmitted through the half-wavelength plate 1003, whereby the polarization plane of the linearly polarized light L rotates by 45 degrees. Then, the linearly polarized light L is transmitted through the Faraday rotator 1004, whereby the polarization plane of the linearly polarized light L further rotates by 45 degrees. Then, the linearly polarized light L is imaged on the mask (not illustrated in FIG. 2) through the objective lens 1005.

In FIG. 3, the linearly polarized light L reflected by the mask (not illustrated in FIG. 3) is incident to the Faraday rotator 1004 through the objective lens 1005. The linearly polarized light L is transmitted through the Faraday rotator 1004, whereby the polarization plane of the linearly polarized light L rotates by 45 degrees. Then, the linearly polarized light L is transmitted through the half-wavelength plate 1003, whereby the polarization plane of the linearly polarized light L rotates by −45 degrees.

Thus, in the example of FIGS. 2 and 3, the light emitted from the light source 1001 is transmitted through the Faraday rotator 1004 twice, whereby the polarization direction of the light rotates by 90 degrees. In FIG. 1, the light emitted from the light source 1001 is reflected by the polarization beamsplitter 1002 and travels toward the mask 1006, and the polarization direction of the light reflected by the mask 1006 rotates by 90 degrees. Therefore, the light is transmitted through the polarization beamsplitter 1002, and travels toward the sensor 1007, not the light source 1001. When the light is incident to the sensor 1007, the sensor 1007 captures the optical image of the mask 1006.

The polarization direction of the light with which the mask 1006 is illuminated changes by both the Faraday rotator 1004 and the half-wavelength plate 1003. At this point, the Faraday rotator 1004 can change an angle of the polarization direction of the light by changing an intensity of the magnetic field applied to the optical material. On the other hand, a rotation mechanism may be provided in the half-wavelength plate 1003 to be able to arbitrarily change the rotation angle. An angle of the optical axis (slow axis) of the half-wavelength plate from the polarization direction of the light being incident into the half-wavelength plate 1003 can be changed by the rotation mechanism. Thereby the polarization direction of the light being emit from the half-wavelength plate 1003 can be varied.

As an example of the Faraday rotator, the magnetic field is applied to the optical material by passing the current through the coil. However, the Faraday rotator is not limited to one in which the electromagnet is used, but a permanent magnet or a combination of the electromagnet and the permanent magnet may be used in the Faraday rotator. An optical refractive index changes substantially linearly according to a temperature. Therefore, in the electromagnet, there is a risk that a temperature distribution is generated in the coil to generate an aberration. On the other hand, the problem can be avoided in the case that the permanent magnet is used. In this case, preferably a type of the permanent magnet or the number of permanent magnets can be varied such that the magnetic field is generated according to the necessary rotation angle. In the combination of the permanent magnet and the electromagnet, the permanent magnet is provided to generate the basic magnetic field, and the magnetic field necessary to generate the necessary rotation angle can be generated by the electromagnet. In this configuration, necessity to exchange the permanent magnet is eliminated, and a temperature rise can minimally be restrained.

Meanwhile, since the Faraday rotator generates the magnetic field, the Faraday effect may occur around the adjacent elements due to the magnetic field leakage from the Faraday rotator. In particular, there is a problem that the Faraday effect occurs in the polarizing beam splitter 1002. This will be described below in detail.

As described above, since the light emitted from the light source 1001 in FIG. 1 is transmitted twice through the Faraday rotator 1004, the deflection direction is rotated by 90 degrees. Accordingly, the light emitted from the light source 1001 is reflected from the polarizing beam splitter 1002 and is directed toward the mask 1006. However, since the deflection direction is rotated by 90 degrees, the light reflected from the mask 1006 is transmitted through the polarizing beam splitter 1002 and is directed toward the sensor 1007 instead of the light source 1001. At this time, the light needs to be transmitted through the polarizing beam splitter 1002 in a state of maintaining the deflection direction rotated by the Faraday rotator 1004. As will be described below, this is because the light scattered by a short defect or an open defect of the mask 1006 is separated from the light scattered by edge roughness and is incident on the sensor 1007.

However, when the Faraday effect occurs in the polarizing beam splitter 1002, the deflection direction of the light is also changed in the polarizing beam splitter 1002. Hence, the light scattered by the edge roughness may be transmitted. Then, in the optical image captured by the sensor 2007, there is no distinction between a brightness and darkness by the short defect or the open defect and a brightness and darkness by the edge roughness, resulting in obstruction in the inspection of patterns of the optical resolution limit or less.

Figure 12:
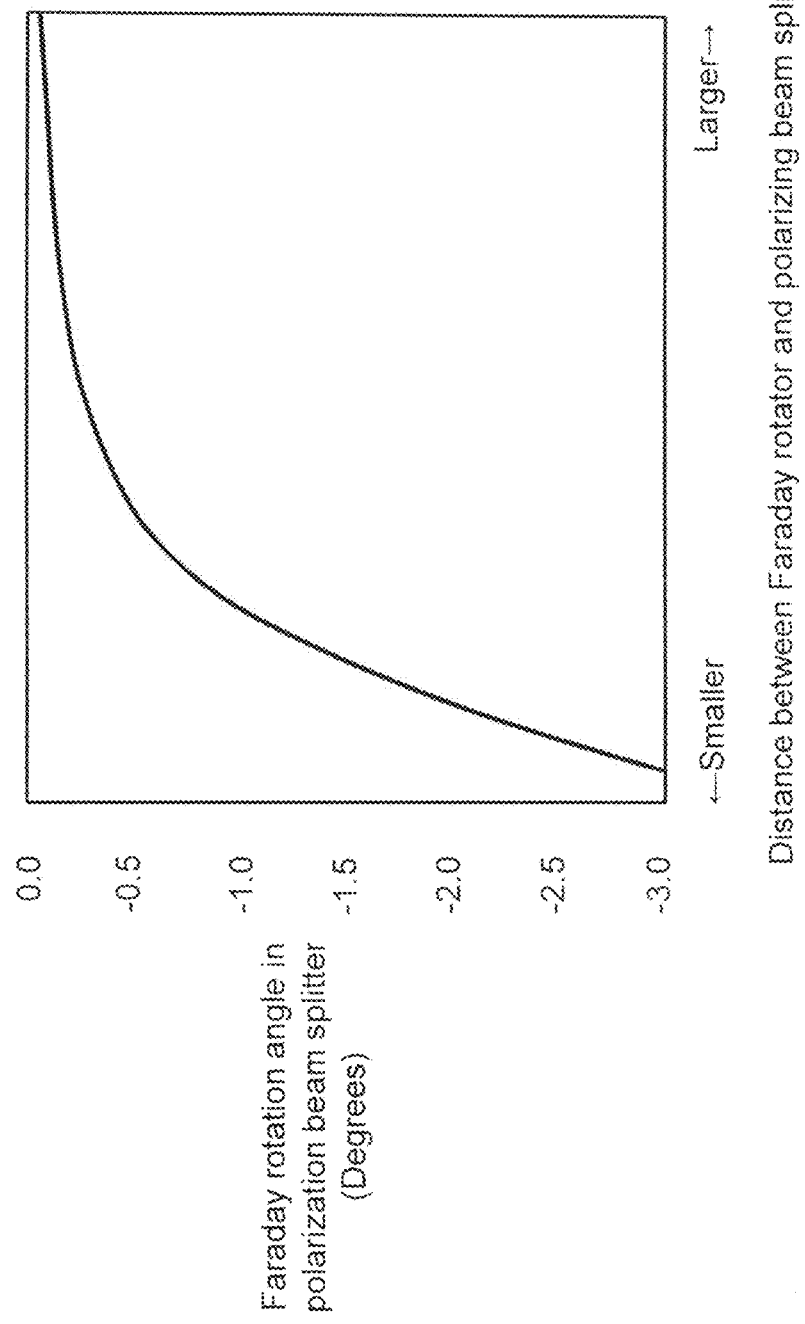
FIG. 12 is an example illustrating a relationship of a distance between the Faraday rotator and the polarizing beam splitter and a Faraday rotation angle in the polarizing beam splitter.

FIG. 12 is an example illustrating a relationship of a distance between the Faraday rotator and the polarizing beam splitter and a Faraday rotation angle in the polarizing beam splitter. Note that the distance can be a length from an end surface of a magnetic optical crystal or a magnet of the Faraday rotator to an end surface of a prism constituting the polarizing beam splitter. As illustrated in FIG. 12, when the distance between the Faraday rotator and the polarizing beam splitter is increased, the Faraday rotation angle in the polarizing beam splitter is decreased. Here, a ratio of change of the Faraday rotation angle is not uniform. For example, in a case where it has the characteristic illustrated in FIG. 12, when the Faraday rotation angle is less than −1.0 degrees, the Faraday rotation angle changes in a manner of a function substantially linear with respect to the distance. When the Faraday rotation angle is larger than −1.0 degrees, the ratio of change is reduced, and when the Faraday rotation angle is equal to or less than −0.5 degrees, the ratio of change is further reduced. When the Faraday rotation angle is equal to or less than −0.2 degrees, the ratio of change is almost unchanged with respect to the distance between the Faraday rotator and the polarizing beam splitter.

Figure 14:
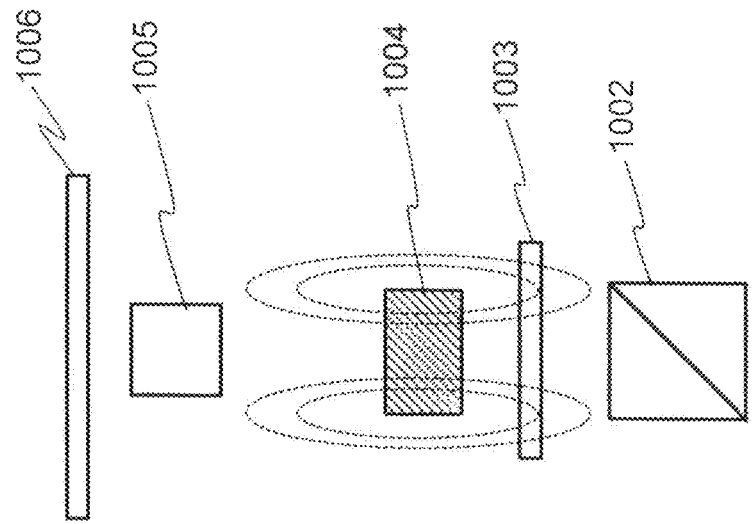
FIG. 14 is another example illustrating the influence of the magnetic field generated by the Faraday rotator on the adjacent optical elements.
Figure 13:
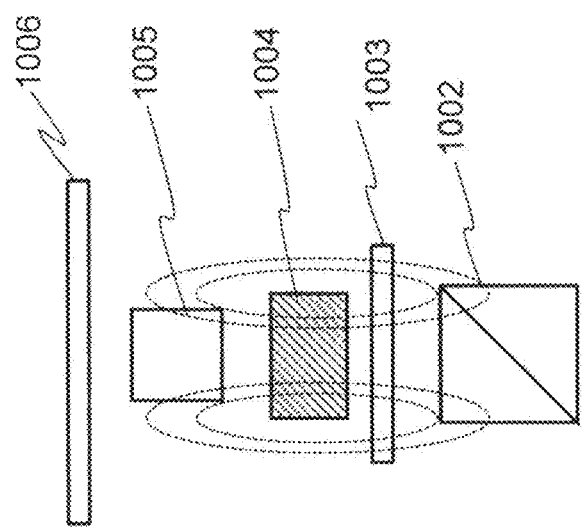
FIG. 13 is an example illustrating the influence of the magnetic field generated by the Faraday rotator on the adjacent optical elements.

FIGS. 13 and 14 schematically illustrate the influence of the magnetic field generated by the Faraday rotator 1004 on the adjacent optical elements. In FIG. 13, the magnetic field of the Faraday rotator 1004 reaches the polarizing beam splitter 1002, the half-wavelength plate 1003, and the objective lens 1005. In contrast, as illustrated in FIG. 14, when the distance between the Faraday rotator 1004 and the adjacent optical element is increased, the influence of the magnetic field of the Faraday rotator is not exerted on the polarizing beam splitter 1002 or the objective lens 1005.

Therefore, in the present embodiment, a predetermined distance is provided between the Faraday rotator 1004 and the adjacent optical element such that the influence of the Faraday rotator 1004 on the adjacent optical element is minimized. At this time, as the distance is increased, the influence on the polarizing beam splitter 1002 is reduced. However, the total size of the imaging apparatus is increased. Therefore, it is preferable to set an appropriate distance in consideration of both. That is, it is preferable that the Faraday rotation angle in the polarizing beam splitter 1002 is 0 degrees; however, as can be seen from FIG. 12, 0 degrees is not realistic because the distance to the Faraday rotator 1004 needs to be considerably increased. Therefore, considering the total size of the imaging apparatus, the Faraday rotator 1004 is disposed away from the polarizing beam splitter 1002 such that an absolute value of the Faraday rotation angle in the polarizing beam splitter 1002 is 0.5 degrees or less, preferably 0.2 degrees or less. In the present configuration, since the light reciprocates through the Faraday rotator, when the Faraday rotation angle is 0 degrees, the ratio at which the light reflected from the object is transmitted through the polarizing beam splitter is 0%. In addition, when the Faraday rotation angle is 45 degrees, the ratio at which the light reflected from the object is transmitted through the polarizing beam splitter is 100%. Therefore, the setting range of the Faraday rotation angle is 0 degrees to 45 degrees. On the other hand, although the Faraday rotation in the optical element has a minor error factor, it is possible to suppress a setting error of the Faraday rotation angle to about 1% by suppressing the Faraday rotation angle to 0.5 degrees or less.

Meanwhile, it is preferable that the influence of the magnetic field of the Faraday rotator 1004 is not exerted on the half-wavelength plate 1003 or the objective lens 1005; however, even when exerted, the Faraday rotation angle can be adjusted by the Faraday rotator 1004, while expecting the Faraday rotation angle occurring accordingly.

On the other hand, the polarizing beam splitter 1002 is disposed to be inclined at 45 degrees with respect to the optical axis of the incident light. Therefore, when the influence of the magnetic field of the Faraday rotator 1004 reaches the polarizing beam splitter 1002, the Faraday rotation angle can be distributed within the polarizing beam splitter 1002. For example, the polarizing beam splitter 1002 can be a cube-shaped beam splitter in which a polarizing film is coated and adhered to an inclined surface of a 45-degrees right-angle prism. However, in this case, although the influence of the magnetic field of the Faraday rotator 1004 reaches the inclined surface close to the Faraday rotator 1004 in FIG. 13, the influence of the magnetic field does not reach the inclined surface away from the Faraday rotator. It is difficult to adjust the distribution of the Faraday rotation angle by a preset Faraday rotation angle of the Faraday rotator 1004. Therefore, a predetermined distance may be provided between the polarizing beam splitter 1002 and the Faraday rotator 1004 such that the influence of the magnetic field of the Faraday rotator 1004 does not reach the polarizing beam splitter 1002.

Figure 4:
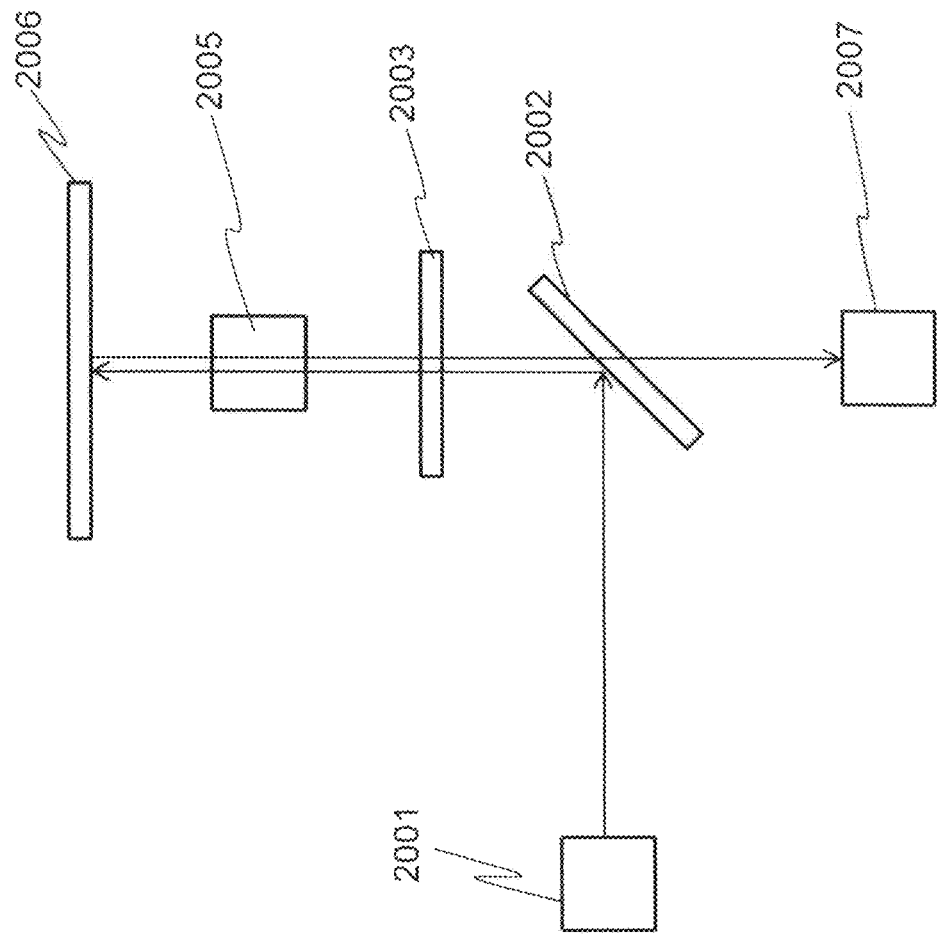
FIG. 4 illustrates an example of an image capturing apparatus that is a comparative example of the present embodiment.

FIG. 4 illustrates an example of an image capturing apparatus that is a comparative example of the present embodiment. In the image capturing apparatus of the comparative example, the light emitted from a light source 2001 is reflected by a half mirror 2002, transmitted through a half-wavelength plate 2003, and is incident to a mask 2006 through a light objective lens 2005. The light reflected by the mask 2006 is incident to the sensor 2007 through the objective lens 2005, the half-wavelength plate 2003, and the half mirror 2002.

Using the image capturing apparatus having the configuration in FIG. 4, the mask 2006 can be illuminated with the light having a polarization characteristic similar to that in FIG. 1, and the light is incident to the sensor 2007. However, in the configuration in FIG. 4, the light amount from the light source 2001 is considerably decreased due to a characteristic of the half mirror 2002. That is, the light amount decreases to a half of the amount of light emitted from the light source 2001 when only the light reflected by the half mirror 2002 is used as the illumination light for the mask 2006. The light amount further decreases to a half when only the light transmitted through the half mirror 2002 in the light reflected from the mask 2006 is used as the light incident to the sensor. Accordingly, for the image capturing apparatus shown in FIG. 4, the light incident to the sensor 2007 becomes a quarter of the amount of light emitted from the light source 2001.

On the other hand, in the image capturing apparatus of the present embodiment shown in FIG. 1, the degradation of the light amount emitted from the light source 1001 can minimally be restrained because the half mirror is not used. Therefore, an adequate amount of the light for performing the inspection can be incident to the sensor 1007. When the image capturing apparatus of the present embodiment is applied to the inspection apparatus, the inspection accuracy can be improved, and the inspection time can be shortened. The image capturing apparatus can also be applied to applications other than the inspection apparatus.

With the progress of microfabrication of the circuit pattern, a pattern size becomes finer than a resolution of the optical system of the inspection apparatus. For example, when a half pitch of the periodic pattern is smaller than 50 nm, the pattern cannot be resolved by the light source in which the DUV light is used. However, in the image capturing apparatus of the present embodiment shown in FIG. 1, the periodic pattern in which the half pitch is smaller than 50 nm can accurately be inspected. The inspection apparatus of the present embodiment will be described below.

Figure 5:
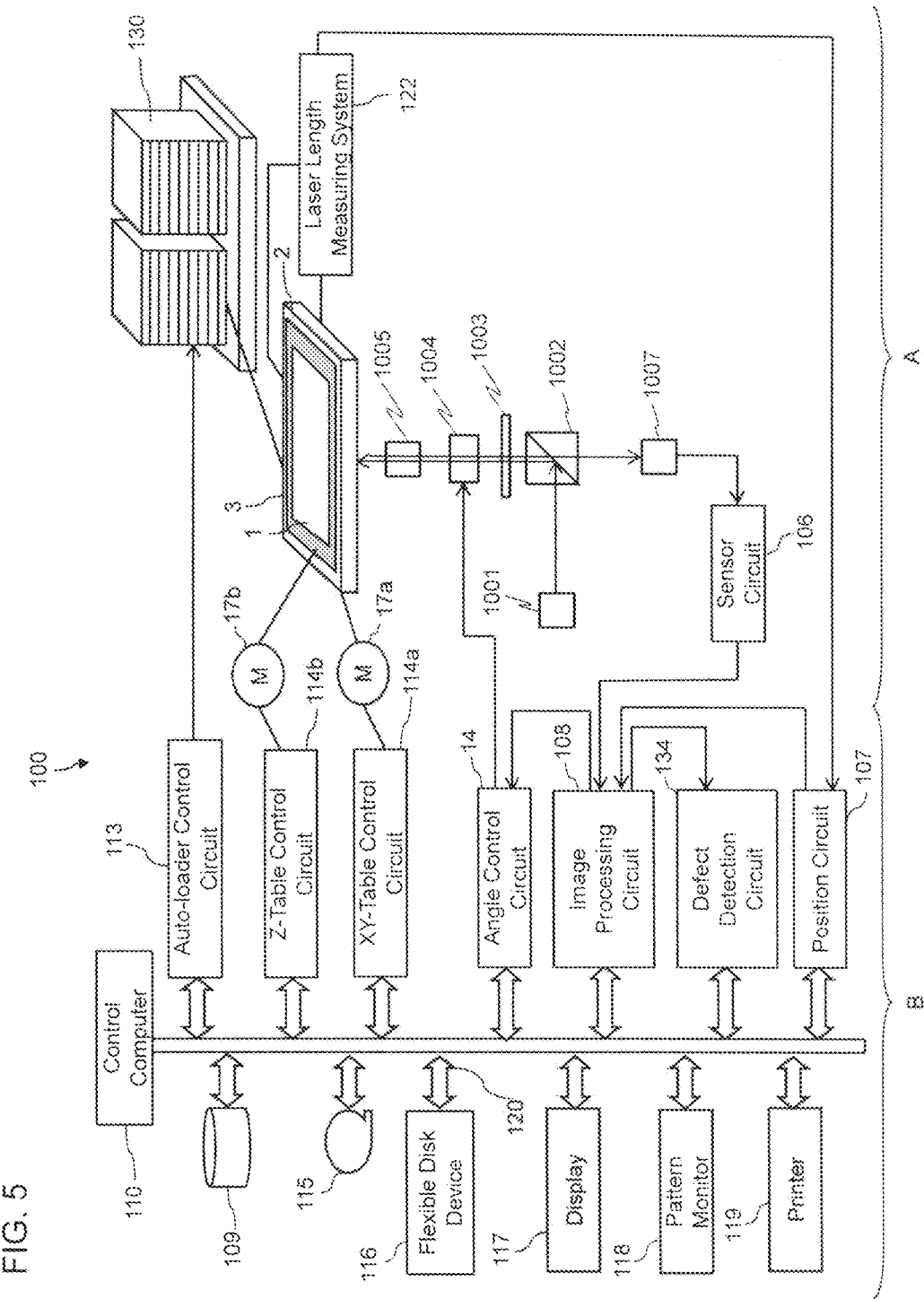
FIG. 5 is a diagram of an inspection apparatus according to the present embodiment.

FIG. 5 is a schematic configuration diagram of an inspection apparatus 100 according to the present embodiment. The inspection apparatus 100 includes an optical unit as shown in FIG. 1. Further, an inspection apparatus 100 includes an optical image acquiring unit A and a control unit B.

Firstly, the optical image acquiring unit A will be described.

In addition to the optical systems in FIG. 1, the optical image generation part A includes a Z-Table 2 that is movable in a vertical direction (Z-direction), an XY-Table 3 that is movable in a horizontal direction (X-direction and Y-direction), a sensor circuit 106, a laser length measuring system 122, and autoloader 130. The XY-Table 3 may have a structure that is movable in the rotation direction.

A sample 1 that is an inspection target is placed on the Z-Table 2. The Z-Table 2 is provided on the XY-Table 3. The mask used in the photolithography technology, and the template used in the nanoimprint technology can be cited as an example of the sample 1.

A repetitive pattern such as a line and space pattern, namely, a regular repetitive pattern having periodicity is formed in the sample 1. At least a part of the pattern is a pattern of an optical resolution limit or less. A pattern formed in a memory mat of a semiconductor chip can be cited as an example of the pattern of the optical resolution limit or less. As used herein, the resolution limit means a resolution limit of the optical system in the inspection apparatus 100, namely, a resolution limit (R=λ/2NA) defined by a wavelength (λ) of the light emitted from the light source 1001 and a numerical aperture (NA) of the objective lens 1005. In the present embodiment, the resolution limit is a value at which at least a part of the pattern formed in the sample 1 is not resolved.

Figure 15:
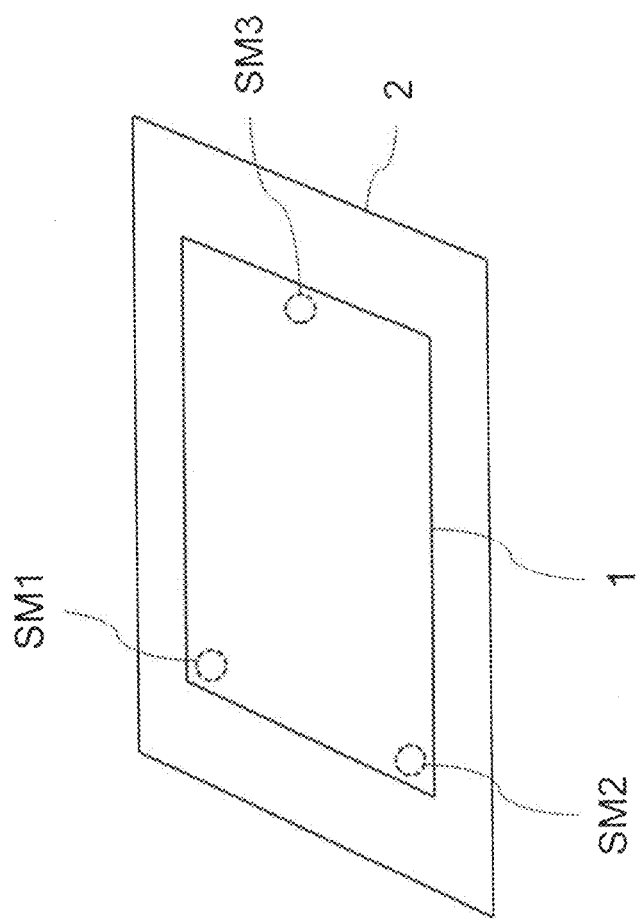
FIG. 15 illustrates the sample is supported at three points by the support member.

Preferably the sample 1 is supported at three points using support members provided in the Z-Table 2. In the case that the sample 1 is supported at four points, it is necessary to adjust a height of the support member with high accuracy. Unless the height of the support member is sufficiently adjusted, there is a risk of deforming the sample 1. On the other hand, in the three-point support, the sample 1 can be supported while the deformation of the sample 1 is suppressed to the minimum. The supporting member is configured by using a ballpoint having a spherical head surface. For example, as shown in FIG. 15 the two support members (SM1, SM2) in the three support members (SM1, SM2, SM3) are in contact with the sample 1 at two corners, which are not diagonal but adjacent to each other in four corners of the sample 1. The remaining support member (SM3) in the three support members (SM1, SM2, SM3) is disposed in the region between the two corners at which the two other support members (SM1, SM2) are not disposed.

The light source 1001 emits the light to the sample 1 in order to generate the optical image of the sample 1. The beam shaping optical system 1008 performs beam shaping to the light emitted from the light source 1001. After that, the light is reflected by the polarization beamsplitter 1002, transmitted through the half-wavelength plate 1003, and is incident to the Faraday rotator 1004. Then the sample 1 is illuminated with the light transmitted through the Faraday rotator 1004 through the objective lens 1005.

The light reflected by the sample 1 is transmitted through the objective lens 1005, the Faraday rotator 1004, the half-wavelength plate 1003, and the polarization beamsplitter 1002, and then enlarged with a predetermined magnification by the imaging optical system 1009, and is incident to the sensor 1007. The sensor 1007 captures the optical image of the mask 1006.

The Faraday rotator 1004 is disposed away from the polarizing beam splitter 1002 such that the Faraday rotation angle in the polarizing beam splitter 1002 is within a range of an angle equal to or larger than −0.5 degrees and an angle equal to or smaller than 0.5 degrees, preferably a range of an angle equal to or larger than −0.2 degrees and an angle equal to or smaller than 0.2 degrees. Accordingly, it is possible to minimize the influence of the magnetic field of the Faraday rotator 1004 on the polarizing beam splitter 1002.

Figure 7:
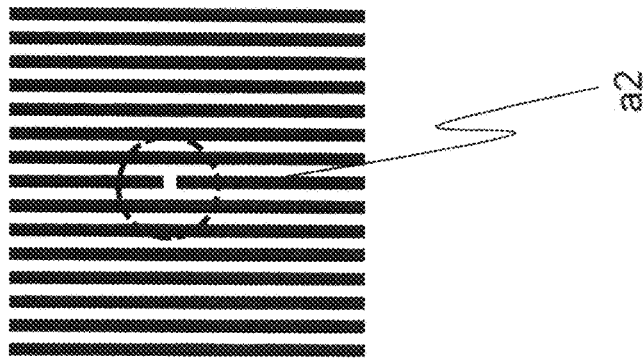
FIG. 7 schematically illustrates an example of the open-circuit defect.
Figure 6:
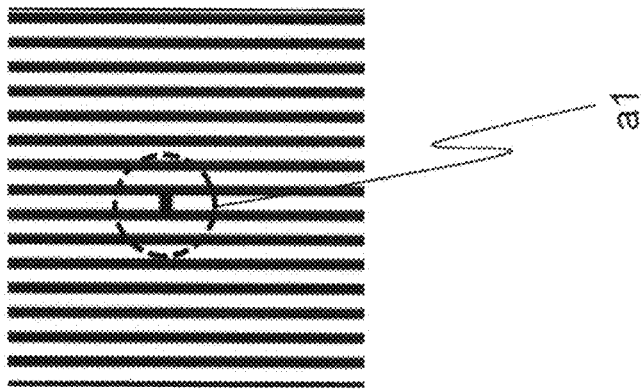
FIG. 6 schematically illustrates an example of the short-circuit defect.

A short-circuit defect in which lines are short-circuited and an open-circuit defect in which the line is disconnected are detected in a pattern of an optical resolution limit or less. FIG. 6 illustrates an example of the short-circuit defect. In a region a1, two lines adjacent to each other are connected to generate the short-circuit defect. FIG. 7 illustrates an example of the open-circuit defect. In a region a2, the line is partially disconnected. Short-circuit defects and open-circuit defects have a serious influence on the performance of the mask. As shown in FIG. 6 and FIG. 7, the black region is several tens of nm lower than the white region when the mask is a template for nanoimprint lithography (NIL).

Figure 8:
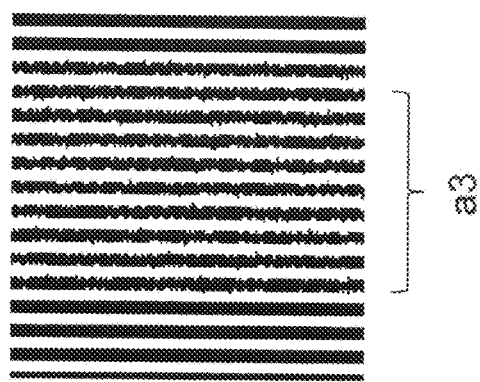
FIG. 8 schematically illustrates a defect caused by edge roughness.

As to another example of pattern defect, edge roughness becomes prominent as illustrated in a region a3 in FIG. 8. However, this defect has a restricted influence on the performance of the mask unlike the short-circuit defect and the open-circuit defect. As shown in FIG. 8, the black region is several tens of nm lower than the white region when the mask is a template for nanoimprint lithography (NIL).

Some defects become practically problematic, and some defects do not become practically problematic. Only the defect becoming practically problematic should be detected in the inspection. Specifically, it is necessary to detect the short-circuit defect and the open-circuit defect, but it is not necessary to detect the edge roughness. However, in the case that the short-circuit defect, the open-circuit defect, and the edge roughness having the size of the optical resolution limit or less are mixed in the pattern of the optical resolution limit or less, more particularly the repetitive pattern having a period of the optical resolution limit or less of the optical system in the inspection apparatus, in observation with the optical system, the brightness and darkness caused by the short-circuit defect or the open-circuit defect is not distinguished from the brightness and darkness caused by the edge roughness. This is because, in the optical image of the pattern, all of the defects, that is, the short-circuit defect, the open-circuit defect, and the edge roughness become blurred by the same amount, that is, these defects are expanded to the same size, namely, to about the size of the optical resolution limit.

Figure 9:
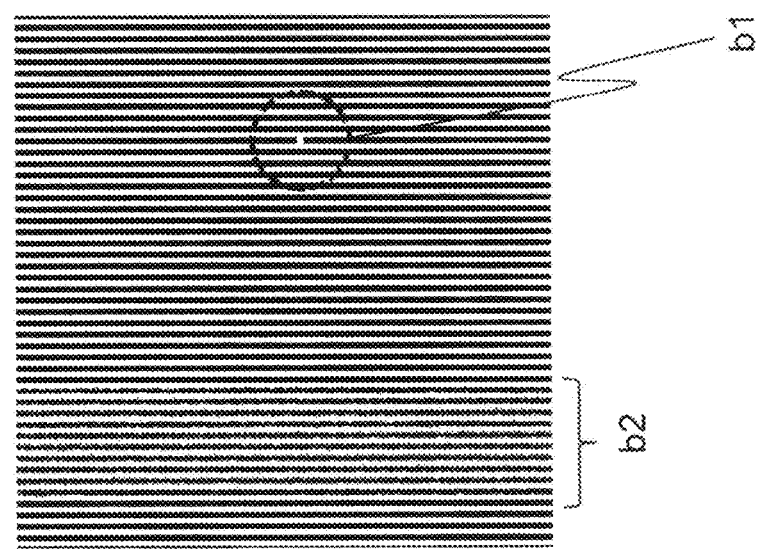
FIG. 9 schematically illustrates the line and space pattern.

FIG. 9 schematically illustrates the line and space pattern provided in the sample that is the inspection target. In FIG. 9, it is assumed that the size of the pattern is smaller than the resolution limit of the optical system. In FIG. 9, the black region is several tens of nm lower than the white region when the mask is a template for nanoimprint lithography (NIL). In the region b1 in FIG. 9, the line pattern is partially lacking thus generating the open-circuit defect. In the region b2, the edge roughness of the line pattern becomes prominent. Although a difference of the defect between the open-circuit defect in the region b1 and the edge roughness in the region b2 is clearly recognized on the actual mask, the differences are hardly distinguished from each other by the observation through the optical system. This is because the optical system behaves as a spatial frequency filter defined by a wavelength λ of the light emitted from the light source and a numerical aperture NA.

Figure 10:
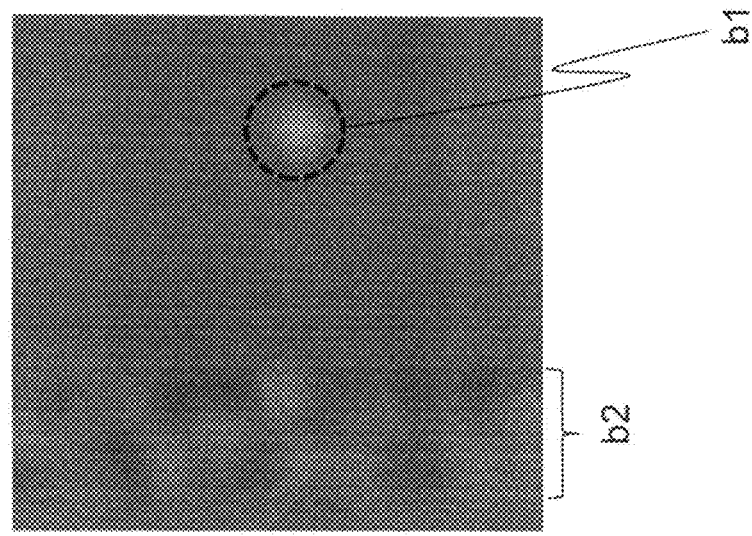
FIG. 10 illustrates a state in which the pattern in FIG. 9 is subjected to the spatial frequency filter.

FIG. 10 illustrates a state in which the pattern in FIG. 9 is subjected to the spatial frequency filter. As can be seen from FIG. 10, the defect in the region b1 and the defect in the region b2 are expanded to the similar size, and the shapes of the defects are hardly distinguishable from each other. Thus, in principle, the open-circuit defect of the optical resolution limit or less and the edge roughness are hardly distinguishable from each other by the optical system. The same holds true for the short-circuit defect and the edge roughness.

The large defect such as the short-circuit defect and the open-circuit defect has the large influence on the polarization state of the illumination light compared with the small defect such as the defect caused by the edge roughness. Specifically, in the short-circuit defect in FIG. 6, a vertical direction and a horizontal direction differ from each other in sensitivity for an electric field component of the illumination light when the adjacent lines are connected to each other.

For example, it is considered that the linearly-polarized light is perpendicularly incident to the mask. When the polarization direction of the linearly-polarized light is 45 degrees with respect to a direction along an edge of the line and space pattern, while a vertical component and a horizontal component of an electric field of the incident light are equal to each other, a difference between the horizontal component and the vertical component of the electric field of the reflected light increases due to the open-circuit defect and the short-circuit defect. As a result, the polarization state of the light reflected from the short-circuit defect differs from that of the incident light.

On the other hand, for the defect caused by the edge roughness in FIG. 8, the lines are not connected to each other, and the lines are not disconnected. Because a size of irregularities in the edge roughness is finer than the short-circuit defect and the open-circuit defect, sensitivity between the vertical and horizontal directions of the electric field component of the illumination light is not so large.

Therefore, in the case that the linearly polarized light is perpendicularly incident to the mask, the polarization direction of the light scattered by the edge roughness becomes a value close to 45 degrees of the polarization direction of the incident light when the linearly polarized light has the polarization direction of 45 degrees with respect to the direction along the edge of the line and space pattern. However, because the direction of edge roughness depends on the direction of the line and space, the vertical direction and the horizontal direction are not completely equal to each other in sensitivity for the polarization, but the polarization direction of the reflected light changes slightly from 45 degrees.

The short-circuit defect or the open-circuit defect differs from the edge roughness in the influence on the polarization state of the illumination light. Accordingly, even if the pattern has the optical resolution limit or less of the optical system, the defect can be classified by taking advantage of the difference. Specifically, by controlling the polarization state of the illumination light and the condition for the polarization control element in the optical system that images the light reflected from the mask, the bright and dark unevenness caused by the edge roughness can be removed with the polarization control element to extract only the change in amplitude of the short-circuit defect or open-circuit defect.

Specifically, in FIG. 5, the rotation angle (Faraday rotation angle θ) of the polarization plane of the light is changed in the Faraday rotator 1004 such that the light scattered by the edge roughness of the sample 1 is reflected by the polarization beamsplitter 1002 and is prevented from being incident to the sensor 1007. The light scattered by the short-circuit defect or the open-circuit defect has a different angle of polarization from the light scattered by edge roughness, which enables the light scattered by the short-circuit defect or the open-circuit defect to transmit to the polarization beamsplitter 1002 and reach the sensor 1007.

Because the short-circuit defect and the open-circuit defect are left in the optical image captured by the sensor 1007 while light-dark unevenness caused by the edge roughness is removed, the short-circuit defect and the open-circuit defect is easily inspected in the optical image. That is, the pattern of the optical resolution limit or less can be inspected using the optical image captured by the sensor 1007.

The Faraday rotation angle θ is changed as follows.

As illustrated in FIGS. 2 and 3, the Faraday rotator 1004 includes the optical material 1004a and the coil 1004b wound around the optical material 1004a. The intensity of the magnetic field applied to the optical material 1004a is controlled by changing the current passed through the coil 1004b, which allows the Faraday rotation angle θ to be changed. At this point, the Faraday rotation angle θ is expressed by the following equation.

$$\theta = VHl$$

Where H is the intensity of the magnetic field, l is a length of a material transmitting the polarized light, and V is a Verdet constant that depends on the kind of material, the wavelength of the polarized light, and temperature.

For example, in the case that a material, such as $SiO_2$, $CaF_2$, and $MgF_2$, which has the high transmittance to the DUV light is used as the optical material 1004a, because the material does not have spontaneous magnetization, it is necessary to apply the large magnetic field to the optical material 1004a in order to obtain the desired Faraday rotation angle θ.

The Faraday rotation angle θ that properly separates the light scattered by the short-circuit defect or the open-circuit defect from the light scattered by the edge roughness depends on the pattern structure. For this reason, in the inspection apparatus 100, the Faraday rotation angle θ is changed according to the pattern of the sample 1. Specifically, an angle control circuit 14 changes the current passed through the coil of the Faraday rotator 1004, and therefore the intensity of the magnetic field applied to the optical material is changed such that the Faraday rotation angle θ is obtained according to the type of the pattern.

In the case that the permanent magnet is used in the Faraday rotator, multiple permanent magnets having different intensities of the magnetic field are prepared. The permanent magnet is selected such that the Faraday rotation angle θ is obtained according to the type of the pattern, and the magnetic field necessary for the optical material is applied.

The Faraday rotation angle θ is also changed by changing a thickness of the optical material. Accordingly, multiple optical materials having different thicknesses are prepared, and the optical material that can achieve the Faraday rotation angle θ corresponding to the type of the pattern may be selected. In this case, the intensity of the magnetic field applied to the optical material can be made uniform irrespective of the Faraday rotation angle provided to the light.

Figure 16:
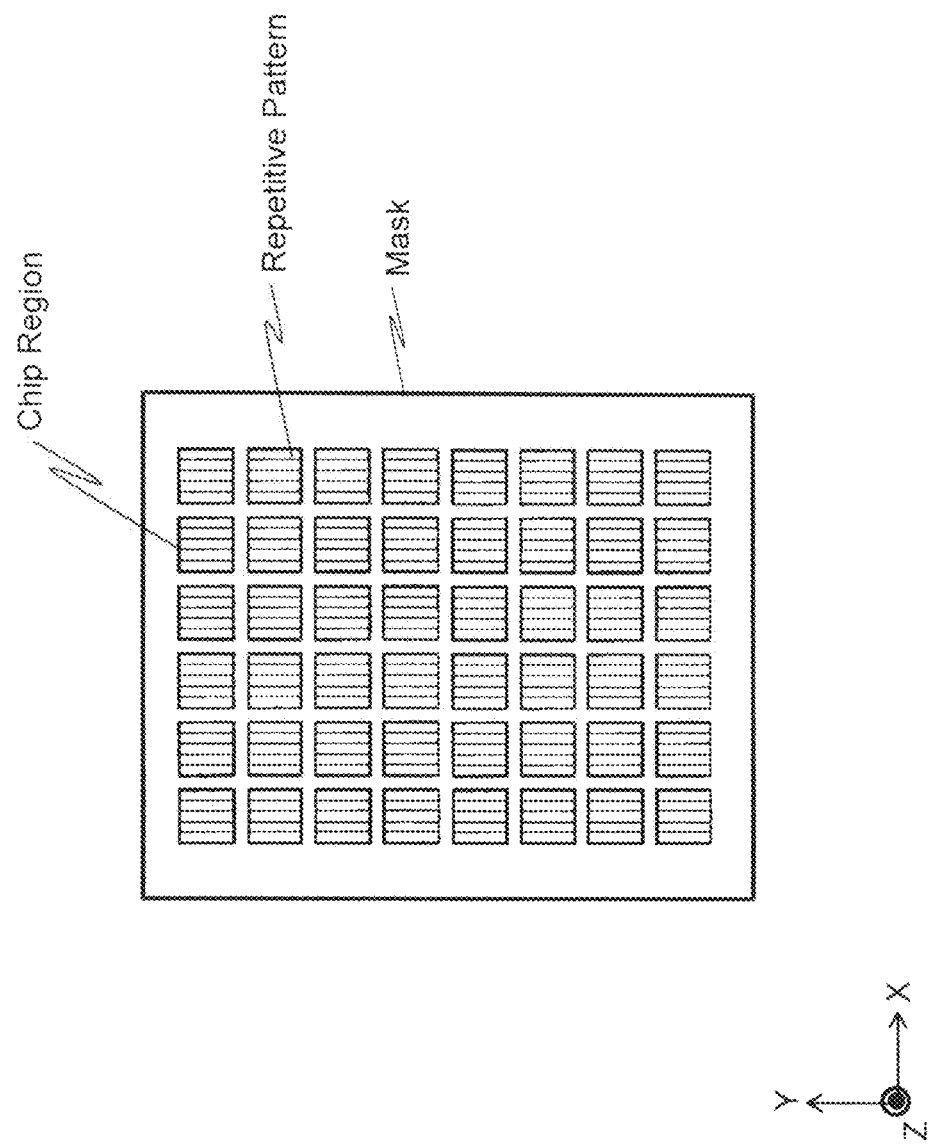
FIG. 16 illustrates a state in which multiple chip regions are arrayed along the X-direction and the Y-direction on a mask.

FIG. 16 illustrates an example in which multiple chip regions are arrayed in the X-direction and the Y-direction. The repetitive pattern is formed in each chip region. For example, the repetitive pattern is a wiring pattern such as the line and space pattern, specifically the pattern in which multiple line portions are arrayed at constant intervals along the X-direction. In this case, the array direction (X-direction) of the line portion is referred to as "a repetitive direction of a repetitive pattern".

For example, when the sample 1 is irradiated with the light having the polarization plane of 45 degrees with respect to the repetitive direction of the repetitive pattern formed in the sample 1, a difference between the large defect such as the short-circuit defect and the open-circuit defect and the small defect such as the edge roughness can emerge in the sensitivity to the electric field component of the light. On the other hand, when the sample 1 is irradiated with the light having the polarization plane of 0 degrees or 90 degrees with respect to the repetitive direction of the repetitive pattern formed in the sample 1, the large defect and the small defect cannot be distinguished from each other because the large defect is equal to the small defect in the light sensitivity. That is, the polarization plane of the light with which the pattern is illuminated is not necessarily 45 degrees with respect to the repetitive direction of the repetitive pattern, but it is necessary that the polarization plane of the light not be 0 degrees or 90 degrees with respect to the repetitive direction of the repetitive pattern. In other words, preferably the polarization plane of the light is set to any angle except an angle within a range of an angle equal to or larger than −0.5 degrees and an angle equal to or smaller than 0.5 degrees, and a range of an angle equal to or larger than −85 degrees and an angle equal to or smaller than 95 degrees.

Figure 17:
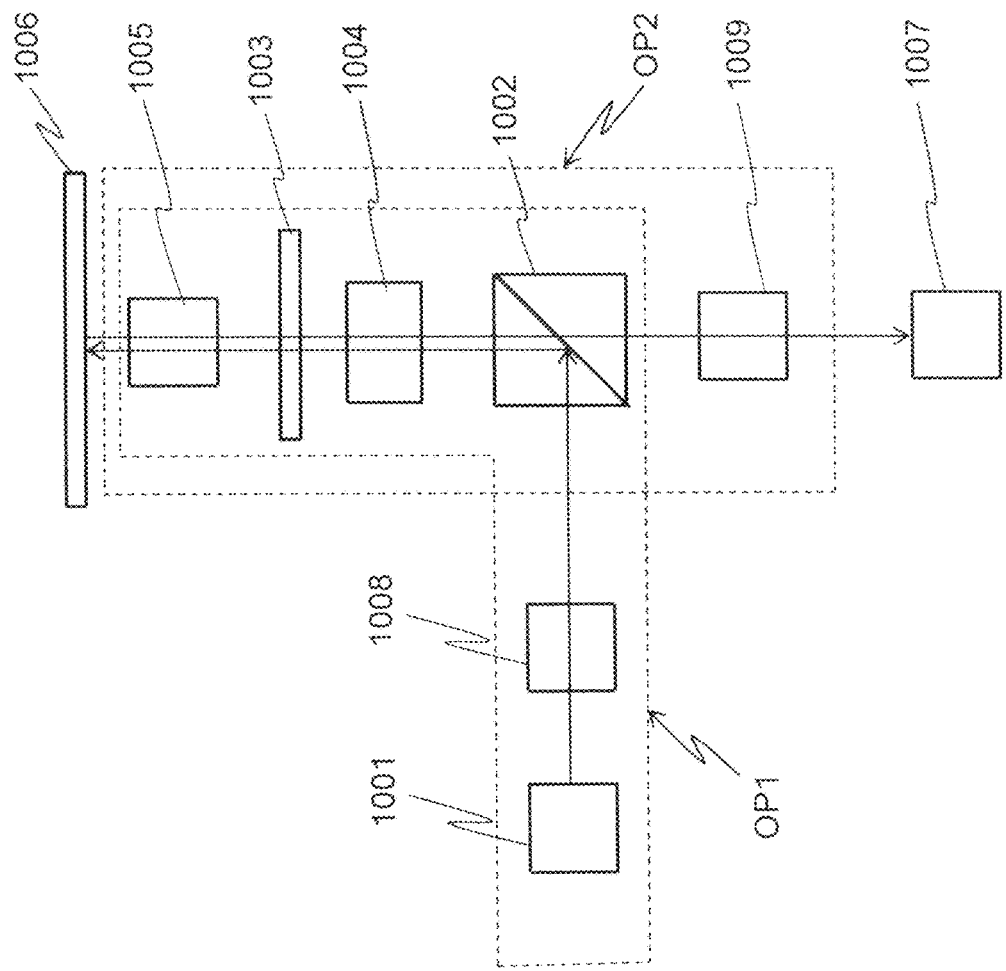
FIG. 17 illustrates another example of a configuration of an image capturing device according to the present embodiment.

The polarization direction of the light with which the mask 1006 is illuminated is changed by not only the Faraday rotator 1004 but also the half-wavelength plate 1003. In the present embodiment, preferably the rotation mechanism is provided in the half-wavelength plate 1003 to rotate the polarization plane of the light at any angle. As shown in FIG. 17, the half-wavelength plate 1003 may be arranged between the Faraday rotator 1004 and the mask 1006, specifically between the Faraday rotator 1004 and the objective lens 1005.

In the present embodiment, a predetermined distance is provided between the Faraday rotator 1004 and the adjacent optical element such that the influence of the Faraday rotator 1004 on the adjacent optical element is minimized. Specifically, the Faraday rotator 1004 is disposed away from the polarizing beam splitter 1002 such that the Faraday rotation angle in the polarizing beam splitter 1002 is within a range of an angle equal to or larger than −0.5 degrees and an angle equal to or smaller than 0.5 degrees, preferably a range of an angle equal to or larger than −0.2 degrees and an angle equal to or smaller than 0.2 degrees.

The above-described configuration can prevent the deflection direction of the light from being changed in the polarizing beam splitter 1002 due to the occurrence of the Faraday effect in the polarizing beam splitter 1002. Therefore, it is possible to prevent the light scattered by the edge roughness from being transmitted through the polarizing beam splitter 1002 and it is possible to accurately inspect the optical image captured by the sensor 1007.

Next, the control unit B as shown in FIG. 5 will be described.

In the control unit B, a control computer 110 that controls the whole inspection apparatus 100 is connected to a position circuit 107, a image processing circuit 108, an angle control circuit 14, a defect detection circuit 134 as a defect detector, an auto-loader control circuit 113, a XY-Table control circuit 114a, Z-Table control circuit 114b, a magnetic disk device 109, a magnetic tape device 115, and flexible disk device 116, which are examples of a storage device, a display 117, a pattern monitor 118, and a printer 119 through a bus 120 that constitutes a data transmission line.

In FIG. 5, the "circuit" is also expressed as the "unit". For example, the image processing circuit 108 corresponds to an image processor of the present invention, and the angle control circuit 14 corresponds to an angle controller of the present invention, further the defect detection circuit 134 corresponds to an a defect detector of the present invention. These components may be constructed with an electric circuit or by a program on a computer. The circuit may also be implemented by not only the program of software but also a combination of hardware and software or a combination of software and firmware. In the case that the circuit is constructed with the program, the program can be recorded in the magnetic disk device 109. For example, each circuit in FIG. 5 may be constructed with the electric circuit or the software that can be processed by the control computer 110. Each circuit in FIG. 5 may be constructed with the combination of the electric circuit and the software. As a more specific example, the defect detection circuit 134, as a detector, may be an apparatus construction, or may be implemented as a software program, or may be implemented as a combination of software and firmware, or software and hardware.

The Z-Table 2 is driven by the motor 17b controlled by the Z-Table control circuit 114b. The XY-Table 3 is driven by the motor 17a controlled by the XY-Table control circuit 114a. A stepping motor, as one example, is used as each motor.

Next, an example of an inspection method using the inspection apparatus 100 will be described.

An example of a specific method for acquiring the optical image of the sample 1 will be described below.

The sample 1 is placed on the Z-Table 2 that is movable in the perpendicular direction. The Z-Table 2 is provided on the XY-Table 3, and the sample 1 is movable in the horizontal direction and the vertical direction by moving the XY-Table 3. A moving position of the XY-Table 3 is measured by the laser length measuring system 122, and sent to the position circuit 107. The sample 1 on the XY-Table 3 is automatically conveyed from the autoloader 130 that is driven by the auto-loader control circuit 113, and the sample 1 is automatically discharged after the inspection is ended.

The light source 1001 emits the light with which the sample 1 is illuminated. The linearly polarized light emitted from the light source 1001 is reflected by the polarization beamsplitter 1002, transmitted through the half-wavelength plate 1003, and is incident to the Faraday rotator 1004. The light transmitted through the Faraday rotator 1004 is imaged onto the sample 1 through the objective lens 1005. A distance between the objective lens 1005 and the sample 1 can be adjusted by vertically moving the Z-Table 2.

Then, the light reflected by the sample 1 is transmitted through the objective lens 1005, the Faraday rotator 1004, the half-wavelength plate 1003, and the polarization beamsplitter 1002, and is incident to the sensor 1007. The sensor 1007 captures the optical image of the mask 1006.

Figure 11:
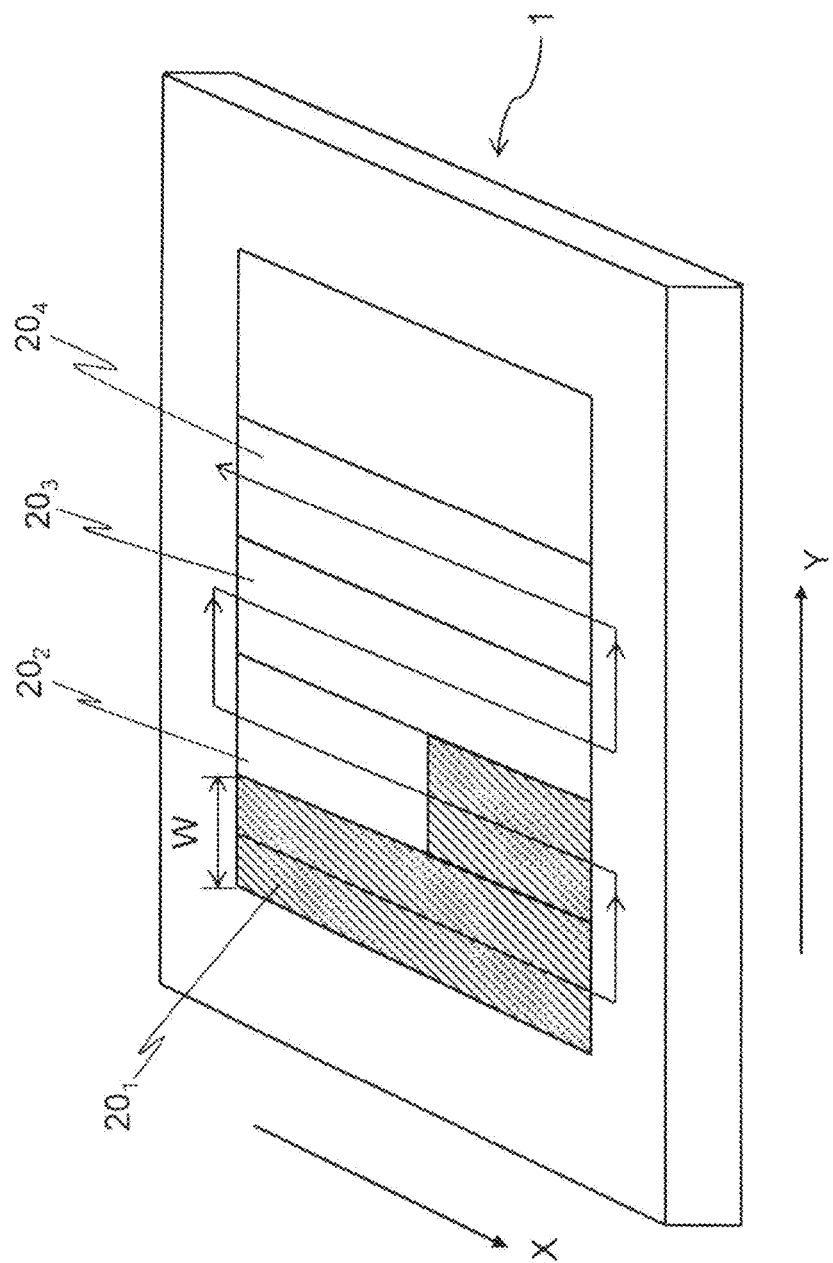
FIG. 11 illustrates a procedure to capture the optical image of a sample.

FIG. 11 is a view illustrating a procedure to capture the optical image of the pattern formed in the sample 1.

As illustrated in FIG. 11, an inspection region on the sample 1 is virtually divided into plural strip-like frames $20_1, 20_2, 20_3, 20_4, \ldots$. The XY-Table control circuit 114a controls motion of the XY-Table 3 in FIG. 5 such that the frames $20_1, 20_2, 20_3, 20_4, \ldots$ are continuously scanned. Specifically, the images having a scan width W in FIG. 11 are continuously input to the sensor 1007 while the XY-Table 3 moves in the −X-direction.

That is, after the image of the first frame $20_1$ is captured, the image of the second frame $20_2$ is captured. In this case, the optical image is captured while the XY-Table 3 moves in the opposite direction (X-direction) to the direction in which the image of the first frame $20_1$ is captured, and the images having the scan width W are continuously input to the sensor 1007. In the case that the image of the third frame $20_3$ is captured, the XY-Table 3 moves in the opposite direction (−X-direction) to the direction in which the image of the second frame $20_2$ is captured, namely, the direction in which the image of the first frame $20_1$ is captured. A hatched-line portion in FIG. 11 schematically expresses the region where the optical image is already captured in the above-mentioned description.

After the pattern images formed in the sensor 1007 are subjected to photoelectric conversion, the sensor circuit 106 performs A/D (Analog to Digital) conversion to the pattern images. Image sensors are arranged in the photodiode array 105. As for the sensor 1007 a line sensor, in which CCD cameras as imaging devices are arranged in line, can be used, as one example. The line sensor includes a TDI (Time Delay Integration) sensor. A pattern of the sample 1 is imaged by the TDI sensor while the XY-table 3 continuously moves in the X-axis direction.

The optical image data, to which the sensor circuit 106 performs the A/D conversion after the image capturing with the sensor 1007, is sent to the image processing circuit 108. In the image processing circuit 108, the optical image data is expressed by the gradation value of each pixel. For example, one of values of a 0 gradation value to a 255 gradation value is provided to each pixel using a gray scale having 256-level gradation value. The optical image data expressed by the gradation value of each pixel is used to inspect the pattern of the optical resolution limit or less in the sample 1.

In the image processing circuit 108, the Faraday rotation angle θ of the Faraday rotator 1004 is set such that the light scattered by the edge roughness in the light from the sample 1 is prevented from being incident to the sensor 1007. Then, the result is sent to the angle control circuit 14, the angle control circuit 14 changes the current passed through the coil of the Faraday rotator 1004, and therefore the intensity of the magnetic field applied to the optical material is changed such that the Faraday rotation angle θ set by the image processing circuit 108 is obtained. At this point, when the sample 1 is illuminated with the light emitted from the light source 1001 again, the light scattered by the short-circuit defect or the open-circuit defect is incident to the sensor 1007 through the half-wavelength plate 1003 and the polarization beamsplitter 1002 while separated from the light scattered by the edge roughness. As a result, in the optical image captured by the sensor 1007, the short-circuit defect and the open-circuit defect are left while the light-dark unevenness caused by the edge roughness is removed. Accordingly, the use of the optical image can inspect the short-circuit defect and the open-circuit defect, namely, the pattern of the optical resolution limit or less.

A specific method for finding the condition that removes the bright and dark unevenness caused by the edge roughness will be described below.

Generally there is a large amount of edge roughness in the whole surface of the mask or template of the inspection target while a small number of short-circuit defects or open-circuit defects exist in the mask or template. For example, when the optical image having the region of 100 μm×100 μm is acquired, there is a small possibility that the short-circuit defect or the open-circuit defect is included in the region, and the small number of defects exist in the region even if the short-circuit defect or the open-circuit defect is included in the region. That is, almost all the optical images in the region are caused by the edge roughness. This means that the condition that removes the defect caused by the edge roughness is obtained from one optical image having the size of about 100 µm×about 100 µm.

As mentioned above, the change in gradation value caused by the edge roughness in the optical image can be removed by controlling the polarization direction of the light incident to the sensor 1007. Specifically, the amount of light that is incident to the sensor 1007, while being scattered by the edge roughness, is changed by controlling the Faraday rotation angle θ using the Faraday rotator 1004, which allows the bright and dark amplitude to be changed in the optical image.

The bright and dark amplitude in the optical image is expressed by a standard deviation of the gradation value in each pixel. For example, assuming that the optical system (described in FIG. 1) has a pixel resolution of 50 nm in the inspection apparatus 100 in FIG. 5, the optical image having the region of 100 µm×100 µm is expressed by 4 million pixels. That is, a specimen of 4 million gradation values is obtained from the one optical image.

For a dark-field illumination system, the standard deviation is obtained with respect to the specimen, the obtained standard deviation is defined as a degree of the scattering light caused by the edge roughness, and the polarization state on the imaging optical system side, namely, the Faraday rotation angle θ is adjusted such that the standard deviation becomes the minimum. Therefore, the amount of scattering light incident to the sensor 1007 due to the edge roughness can be minimized.

For the optical image in a bright-field optical system, a degree of the brightness and darkness caused by the edge roughness is influenced by zero-order light. The reason is as follows. Because the fine periodic pattern of the optical resolution limit or less exists in the inspection target, the polarization state of the zero-order light changes due to a phase-difference effect caused by structural birefringence. Therefore, the light amount that becomes a base light amount also changes when the Faraday rotation angle is changed in order to remove the reflected light caused by the edge roughness. Because the bright-field image is a product of an electric field amplitude of the scattering light from the short-circuit defect, the open-circuit defect, or the edge roughness and an electric field amplitude of the zero-order light, the degree of the brightness and darkness caused by the edge roughness is influenced by an intensity of the zero-order light.

In order to remove the influence of the scattering light due to the edge roughness to improve the detection sensitivity for the short-circuit defect or open-circuit defect, it is necessary to find, not the condition in which a function (specifically, a function expressing the electric field amplitude of the zero-order light) caused by the zero-order light becomes the minimum, but the condition that a function caused by the edge roughness (specifically, a function expressing the electric field amplitude of the scattering light caused by the edge roughness) becomes the minimum. The reason the function caused by the zero-order light becomes the minimum is that the function caused by the zero-order light is the condition that the base light amount becomes the minimum but the influence of the edge roughness is not completely removed.

The function caused by the edge roughness becoming the minimum is obtained by a calculation using a standard deviation a of the gradation value of the optical image and an average gradation value A. The standard deviation a includes various noise factors, and particularly the standard deviation a is largely influenced by the brightness and darkness caused by the edge roughness. The average gradation value A of the optical image is the base light amount, namely, the intensity of the zero-order light. The electric field amplitude of the scattering light due to the edge roughness is proportional to a value in which the standard deviation σ of the optical image is divided by a square root of the average gradation value A. In order to find the condition that minimizes the bright and dark amplitude caused by the edge roughness, the optical image is acquired while the angle θ of the half-wavelength plate 1007 is changed, and the value (σ/√A) in which the standard deviation of the gradation value in the obtained optical image is divided by the square root of the average gradation value is calculated. The angle θ is obtained when the value (σ/√A) becomes the minimum.

As mentioned above, for the large defect such as the short-circuit defect and the open-circuit defect, the vertical direction and the horizontal direction differ from each other in the sensitivity to the electric field component of the illumination light. Accordingly, when the electric field amplitude of the scattering light caused by the large defect becomes the minimum, the Faraday rotation angle θ differs from that of the scattering light caused by the edge roughness. That is, even if the Faraday rotation angle θ is applied when the electric field amplitude of the scattering light caused by the edge roughness becomes the minimum, the electric field amplitude of the scattering light caused by the short-circuit defect or the open-circuit defect does not become the minimum. Therefore, the short-circuit defect and the open-circuit defect can be detected without being buried in the amplitude of the brightness and darkness caused by the edge roughness.

As described above the Faraday rotation angle θ that properly separates the light scattered by the short-circuit defect or the open-circuit defect from the light scattered by the edge roughness depends on the pattern structure. The detail is described as follows.

When the electric field amplitude of the scattering light caused by the edge roughness becomes the minimum, the Faraday rotation angle θ depends on a structure of the pattern formed in the inspection target. For example, Faraday rotation angle θ at which the electric field amplitude of scattering light caused by edge roughness becomes the minimum also changes when a pitch, a depth, or a line and space ratio of the pattern changes. Accordingly, it is necessary to obtain the Faraday rotation angle θ according to the structure of the pattern of the inspection target. In the case that the identical pattern is provided in all inspection targets, the previously obtained angle θ can continuously be used. On the other hand, in the case that the patterns of inspection targets vary from one target to another target, it is necessary to change the Faraday rotation angle θ according to the inspection target. Additionally, even in the identical design pattern, the depth or the line and space ratio is slightly changed by various error factors, and possibly the Faraday rotation angle θ of the half-wavelength plate 1007, which minimizes the electric field amplitude of the scattering light, varies from one target to another target. In this case, it is necessary to follow the variation to change the Faraday rotation angle θ for each individual inspection target, even if the inspection target has an identical pattern.

Thus, the condition that removes the bright and dark unevenness caused by the edge roughness, namely, the angle of the Faraday rotation angle θ can be obtained. This processing is performed at a stage prior to the inspection of the sample 1. That is, in order to find the condition that removes the defect caused by the edge roughness, the sensor 1007 captures the optical image of the sample 1 while the angle of the Faraday rotation angle θ is changed. Specifically, the angle control circuit 14 changes the current passed through the coil 1004b of the Faraday rotator 1004, and therefore the intensity of the magnetic field applied to the optical material is changed such that the predetermined Faraday rotation angle θ is obtained. For example, one optical image having the size of about 100 μm×about 100 μm may be obtained in each predetermined value of the Faraday rotation angle θ. The generated data of the optical image is sent to the image processing circuit 108 through the sensor circuit 106, and the Faraday rotation angle θ of the Faraday rotator 1004 is set such that the light scattered by the edge roughness in the light from the sample 1 is prevented from being incident to the sensor 1007.

As described above, the optical image data is expressed by the gradation value of each pixel in the image processing circuit 108. Therefore, in the dark-field illumination system, the standard deviation is obtained with respect to one optical image. The obtained standard deviation is defined as the degree of the scattering light caused by the edge roughness, and the Faraday rotation angle θ is obtained such that the standard deviation becomes the minimum. On the other hand, in the bright-field illumination system, the image processing circuit 108 obtains the standard deviation σ and the average gradation value A of the gradation value. The optical image is acquired while the Faraday rotation angle θ is changed, the value in which the standard deviation σ of the gradation value in the acquired optical image is divided by the square root of the average gradation value A is calculated, and the Faraday rotation angle θ is obtained when the value becomes the minimum.

Information on the Faraday rotation angle θ obtained by the image processing circuit 108 is sent to the angle control circuit 14. The angle control circuit 14 controls the current passed through the coil 1004b of the Faraday rotator 1004 according to the information from the image processing circuit 108. Therefore, the intensity of the magnetic field applied to the optical material of the Faraday rotator 1004 can be changed to set the Faraday rotation angle θ to the value obtained by the image processing circuit 108.

The Faraday rotation angle θ is set to the value obtained by the image processing circuit 108, whereby the light scattered by the edge roughness is prevented from being incident to the sensor 1007. Therefore, the light scattered by the short-circuit defect or the open-circuit defect is incident to the sensor 1007 through the half-wavelength plate 1003 and the polarization beamsplitter 1002 while separated from the light scattered by the edge roughness. In the optical image captured by the sensor 1007, the short-circuit defect and the open-circuit defect are left while the light-dark unevenness caused by the edge roughness is removed. Accordingly, the use of the optical image can inspect the short-circuit defect and the open-circuit defect, namely, the pattern of the optical resolution limit or less.

In the image processing circuit 108, the image data in the optical image (in which the defect caused by the edge roughness is removed) is expressed by the gradation value of each pixel.

The information on the gradation value obtained by the image processing circuit 108 is sent to the defect detection circuit 134. When the short-circuit defect or the open-circuit defect exists in the repetitive pattern of the optical resolution limit or less of the optical system, an irregularity is generated in the regularity of the pattern, the gradation value in the location where the defect exists varies from the surrounding gradation value. Therefore, the short-circuit defect or the open-circuit defect can be detected. Specifically, for example, the defect detection circuit 134 has thresholds above and below the average gradation value, and the location is recognized as the defect when the gradation value sent from the image processing circuit 108 exceeds the threshold. The threshold level is set in advance of the inspection. For example, the defect information obtained by the defect detection circuit 134 is stored in the magnetic disk device 109.

The inspection apparatus 100 can also have a review function in addition to the inspection function. As used herein, the review refers to an operation in which an operator determines whether the detected defect becomes a problem.

For example, a coordinate of a place determined to be the defect by the defect detection circuit 134 and the optical image are sent to a review device (not illustrated). An operator reviews the optical image by comparison with a standard image that is a model image. The defect information determined by the review can be stored as a defect information list in the magnetic disk device 109. For example, a reference image produced by design data of the inspection target pattern is used as the standard image.

According to the present embodiment, the use of the Faraday rotator instead of the half mirror provides the image capturing apparatus that can minimally restrain the degradation of the light amount in the reflective illumination optical system to capture the image of the object. The use of the image capturing device provides the inspection apparatus and inspection method, for being able to minimally restrain the degradation of the light amount in the reflective illumination optical system to capture the image of the inspection target, which allows the inspection to be performed with high accuracy.

According to the present embodiment, the pattern of the optical resolution limit or less can be inspected by changing the Faraday rotation angle θ. By providing a predetermined distance between the Faraday rotator and the adjacent optical element such that the influence of the Faraday rotator on the adjacent optical element is minimized, it is possible to prevent the deflection direction of the light from being changed by the adjacent optical element due to the occurrence of the Faraday effect in the adjacent optical element. Therefore, since it is possible to prevent the light scattered by the edge roughness from being incident on the sensor, the optical image captured by the sensor can be inspected. That is, the fine pattern of the optical resolution limit or less can be inspected according to the inspection apparatus and inspection method of the present embodiment.

The present invention is not limited to the embodiment described and can be implemented in various ways without departing from the spirit of the invention.

In the above embodiments, the sample is illuminated with the light emitted from the light source, and the light reflected from the sample is incident to the sensor to capture the optical image. Alternatively, the light transmitted through the sample may be incident to the sensor to capture the optical image. The above description of the present embodiment has not specified apparatus constructions, control methods, etc., which are not essential to the description of the invention, since any suitable apparatus construction, control methods, etc. can be employed to implement the invention. Further, the scope of this invention encompasses all image capturing apparatuses, inspection apparatus and inspection methods employing the elements of the invention and variations thereof, which can be designed by those skilled in the art.

What is claimed is:

1. An image capturing apparatus comprising:
a light source configured to emit light having a predetermined wavelength;
a polarizing beam splitter configured to receive the light from the light source;
a Faraday rotator configured to rotate a polarization plane of the light forwarded by the polarizing beam splitter by a rotation angle, the rotation angle being accommodated to a pattern formed in a target to distinguish one or more types of defects of interest in the pattern for image capturing;
an objective lens configured to illuminate the target with the light; and
a sensor configured to
capture an optical image of the target by causing the light reflected by the target to be incident through the objective lens, the Faraday rotator, and the polarizing beam splitter, and
capture the optical image of the pattern of the target from the reflected light which is generated by illuminating the target with the light having the polarization plane rotated by the Faraday rotator by the accommodated rotation angle,
wherein the Faraday rotator is provided between the polarizing beam splitter and the target and disposed a predetermined distance from the polarizing beam splitter, the predetermined distance being a distance for which a Faraday rotation angle due to a Faraday effect occurring in the polarizing beam splitter is any angle within a range from −0.5 degrees to 0.5 degrees.

2. The image capturing apparatus according to claim 1, wherein the Faraday rotator is disposed away from the polarizing beam splitter such that the Faraday rotation angle due to the Faraday effect occurring in the polarizing beam splitter is within a range of an angle equal to or larger than −0.2 degrees and an angle equal to or smaller than 0.2 degrees.

3. The image capturing apparatus according to claim 1, wherein the magnetic field is applied to the Faraday rotator such that a polarization plane of the light rotates 90 degrees by transmitting the light back and forth through the Faraday rotator.

4. The image capturing apparatus according to claim 1, further comprising:
a half-wavelength plate between the polarizing beam splitter and the target,
wherein the half-wavelength plate changes a polarization direction of the light with which the target is illuminated.

5. The image capturing apparatus according to claim 4, wherein
the half-wavelength plate includes a rotation mechanism, and
the rotation mechanism changes the polarization direction of the light by changing an angle of the optical axis of the half-wavelength plate.

6. An inspection apparatus comprising:
an illumination optical system including a light source configured to emit light having a predetermined wavelength, a polarizing beam splitter configured to receive the light emitted from the light source, a Faraday rotator configured to rotate a polarization plane of the light forwarded by the polarizing beam splitter by a rotation angle, the rotation angle being accommodated to a pattern formed in a target to distinguish one or more types of defects of interest in the pattern for image capturing, and an objective lens configured to illuminate the target with the light;
a sensor configured to
capture an optical image of the pattern formed in the target by causing the light reflected by the target to be incident through the objective lens, the Faraday rotator, and the polarizing beam splitter, and
capture the optical image of the target from the reflected light which is generated by illuminating the target with the light having the polarization plane rotated by the Faraday rotator by the accommodated rotation angle; and
a defect detector configured to detect the one or more types of defects of interest in the pattern of the target based on the optical image which is captured while the polarization plane of light incident to the Faraday rotator is rotated by the accommodated rotation angle,
wherein the predetermined wavelength of the light from the light source and a numerical aperture of an objective lens through which the target is illuminated with the light transmitted through the Faraday rotator defines a resolution limit, wherein the resolution limit is a value at which the pattern is not resolved, and
wherein the Faraday rotator is provided between the polarizing beam splitter and the target and disposed a predetermined distance from the polarizing beam splitter, the predetermined distance being a distance for which a Faraday rotation angle due to a Faraday effect occurring in the polarizing beam splitter is any angle within a range from −0.5 degrees to 0.5 degrees.

7. The inspection apparatus according to claim 6, wherein the Faraday rotator is disposed away from the polarizing beam splitter such that the Faraday rotation angle due to the Faraday effect occurring in the polarizing beam splitter is within a range of an angle equal to or larger than −0.2 degrees and an angle equal to or smaller than 0.2 degrees.

8. The inspection apparatus according to claim 6, wherein the magnetic field is applied to the Faraday rotator such that a polarization plane of the light rotates 90 degrees by transmitting the light back and forth through the Faraday rotator.

9. The inspection apparatus according to claim 6, further comprising:
a half-wavelength plate between the polarizing beam splitter and the target,
wherein the half-wavelength plate changes a polarization direction of the light with which the target is illuminated.

10. The inspection apparatus according to claim 9, wherein
the half-wavelength plate includes a rotation mechanism, and
the rotation mechanism changes the polarization direction of the light by changing an angle of the optical axis of the half-wavelength plate.

11. An inspection method comprising:
reflecting light emitted from the light source which emits the light having a predetermined wavelength by a polarizing beam splitter,
transmitting the light through a Faraday rotator configured to rotate a polarization plane of the light forwarded by the polarizing beam splitter by a rotation angle, the rotation angle being accommodated to a pattern formed in a target to distinguish one or more types of defects of interest in the pattern for inspection, and an objective lens configured to illuminate the target with the light, transmitting the light reflected by the target through the objective lens, the Faraday rotator, and the polarizing beam splitter, imaging the light on a sensor to capture an optical image of a pattern formed in the target, and detecting the one or more types of defects of interest in the pattern of the target based on the optical image which is captured while the polarization plane of light incident to the Faraday rotator is rotated by the accommodated rotation angle, wherein the predetermined wavelength of the light from the light source and a numerical aperture of the objective lens defines a resolution limit, wherein the resolution limit is a value at which the pattern is not resolved, and wherein the Faraday rotator is provided between the polarizing beam splitter and the target and disposed a predetermined distance from the polarizing beam splitter, the predetermined distance being a distance for which a Faraday rotation angle due to a Faraday effect occurring in the polarizing beam splitter is any angle within a range from −0.5 degrees to 0.5 degrees.

12. The inspection method according to claim 11, wherein the Faraday rotator is disposed away from the polarizing beam splitter such that the Faraday rotation angle due to the Faraday effect occurring in the polarizing beam splitter is within a range of an angle equal to or larger than −0.2 degrees and an angle equal to or smaller than 0.2 degrees.

13. The inspection method according to claim 11, wherein the magnetic field is applied to the Faraday rotator such that a polarization plane of the light rotates 90 degrees by transmitting the light back and forth through the Faraday rotator.

14. The inspection method according to claim 11, further comprising:

a half-wavelength plate between the polarizing beam splitter and the target, wherein the half-wavelength plate changes a polarization direction of the light with which the target is illuminated.

15. The inspection method according to claim 11, wherein the half-wavelength plate includes a rotation mechanism, and the rotation mechanism changes the polarization direction of the light by changing an angle of the optical axis of the half-wavelength plate.

16. The image capturing apparatus according to claim 1, wherein the sensor is configured to capture the optical image of the one or more types of defects of interest in the pattern formed in the target which is smaller than a resolution limit defined by the predetermined wavelength of the light from the light source and a numerical aperture of the objective lens.

17. The image capturing apparatus according to claim 16, wherein the one or more types of defects of interest in the pattern formed in the target includes a short-circuit defect and an open-circuit defect.

18. The inspection apparatus according to claim 6, wherein the sensor is configured to capture the optical image of the one or more types of defects of interest in the pattern formed in the target which is smaller than a resolution limit defined by the predetermined wavelength of the light from the light source and a numerical aperture of the objective lens.

19. The inspection apparatus according to claim 18, wherein the one or more types of defects of interest in the pattern formed in the target includes a short-circuit defect and an open-circuit defect.

20. The inspection method according to claim 11, wherein the imaging the light on the sensor to capture the optical image of the pattern includes capturing the optical image of the one or more types of defects of interest in the pattern formed in the target which is smaller than a resolution limit defined by the predetermined wavelength of the light from the light source and a numerical aperture of the objective lens.

* * * * *